United States Patent
Kim-Shapiro et al.

(10) Patent No.: US 8,980,871 B2
(45) Date of Patent: Mar. 17, 2015

(54) METHODS OF TREATMENT FOR HEMOLYSIS

(75) Inventors: Daniel B. Kim-Shapiro, Winston-Salem, NC (US); S. Bruce King, Walnut Cove, NC (US); Daniel A. Sweeney, Laurel, MD (US); Mark T. Gladwin, Garrett Park, MD (US)

(73) Assignees: Wake Forest University Health Sciences, Winston-Salem, NC (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 574 days.

(21) Appl. No.: 12/678,539

(22) PCT Filed: Sep. 19, 2008

(86) PCT No.: PCT/US2008/010950
§ 371 (c)(1),
(2), (4) Date: Jun. 3, 2010

(87) PCT Pub. No.: WO2009/038796
PCT Pub. Date: Mar. 26, 2009

(65) Prior Publication Data
US 2010/0239692 A1    Sep. 23, 2010

Related U.S. Application Data

(60) Provisional application No. 60/973,878, filed on Sep. 20, 2007.

(51) Int. Cl.
A61K 31/33 (2006.01)
A01N 43/00 (2006.01)
A61K 31/58 (2006.01)

(52) U.S. Cl.
CPC ............................ *A61K 31/58* (2013.01)
USPC ...... 514/183; 514/248; 514/255.05; 514/256; 514/263.22; 514/269; 544/235; 544/277; 544/295; 544/319; 544/326; 544/328

(58) Field of Classification Search
None
See application file for complete search history.

(56) References Cited

U.S. PATENT DOCUMENTS

| 6,936,639 | B2 | 8/2005 | Wink et al. | |
| 7,045,152 | B2 | 5/2006 | Stamler | |
| 2005/0101659 | A1* | 5/2005 | Haynes, Jr. | 514/443 |
| 2007/0154569 | A1 | 7/2007 | Gladwin et al. | |
| 2007/0191377 | A1 | 8/2007 | Worcel | |

FOREIGN PATENT DOCUMENTS

| WO | WO 2004/054433 A2 | 7/2004 |
| WO | WO 2005046661 A2 * | 5/2005 |
| WO | WO 2005107384 A2 * | 11/2005 |

OTHER PUBLICATIONS

Grubina et al, Journal of Biological Chemistry, vol. 282, No. 17, Apr. 27, 2007, pp. 12916-12927.*
King et al, Current Topics in Medicinal Chemistry, 2005, 5, 665-76.*
Doyle MP et al. Oxidation and reduction of hemoproteins by trioxodinitrate(II). The role of nitrosyl hydride and nitrite. J. Am. Chem. Soc. 1988; 110: 593-599.
Butler AR et al. Diffusion of nitric oxide and scavenging by blood in the vasculature. Biochimica et Biophysica Acta. 1998; 1425: 168-176.
Doherty DH Rate of reaction with nitric oxide determines the hypertensive effect of cell-free hemoglobin. Nature Biotechnology. Jul. 1998; 16: 672-676.
Gulati A et al. Pharmacology of hemoglobin therapeutics. J Lab Clin Med. 1999; 133(2): 112-119.
Liao JC et al. Intravascular flow decreases erythrocyte consumption of nitric oxide. Proc Natl Acad Sci USA. Jul. 1999; 96: 8757-8761.
Vaughn MW et al. Erythrocytes possess an intrinsic barrier to nitric oxide consumption. The Journal of Biological Chemistry. 2000; 275(4): 2342-2348.
Huang KT et al. Modulation of nitric oxide bioavailability by erythrocytes. PNAS. Sep. 25, 2001; 98(20): 11771-11776.
Reiter CD et al. Cell-free hemoglobin limits nitric oxide bioavailability in sickle-cell disease. Nature Medicine. Dec. 2002; 8(12): 1383-1389.
Miranda KM et al. Comparison of the reactivity of nitric oxide and nitroxyl with heme proteins. A chemical discussion of the differential biological effects of these redox related products of NOS. Journal of Inorganic Biochemistry. 2003; 93: 52-60.
Miranda KM et al. A biochemical rationale for the discrete behavior of nitroxyl and nitric oxide in the cardiovascular system. PNAS. Aug. 5, 2003; 100(16): 9196-9201.

(Continued)

*Primary Examiner* — Wu-Cheng Winston Shen
*Assistant Examiner* — Jean Cornet
(74) *Attorney, Agent, or Firm* — Myers Bigel Sibley & Sajovec, P.A.

(57) ABSTRACT

Provided herein are methods of treating hemolysis by administering an active compound in an amount sufficient to treat said hemolysis. It has been found that nitroxyl donors or similar compounds preferentially react with cell-free OxyHb, as compared to OxyHb encapsulated in a red blood cell, and reacts with MetHb to form iron-nitrosyl Hb or nitrite bound MetHb. It has also been found that such compounds reduce cell-free Hb and hemolysis. Active compounds are also contemplated for use in combination therapies, for example, in combination with the administration of red blood cells and/or an agent that promotes hematopoiesis, or in combination with the administration of a nitric oxide donor.

17 Claims, 14 Drawing Sheets

(56) References Cited

OTHER PUBLICATIONS

Gladwin MT and Schechter AN. NO contest: nitrite versus s-nitrosohemoglobin. Cir. Res. 2004; 94: 851-855.

Kim-Shapiro DB et al. How do red blood cells dilate blood vessels? Circulation Research. 2004; 95: e10.

Olson JS et al. Serial review: biomedical implications for hemoglobin interactions with nitric oxide. Free Radical Biology & Medicine. 2004; 36(6): 685-697.

Wang X et al. Biological activity of nitric oxide in the plasmatic compartment. PNAS. Aug. 3, 2004; 101(31): 11477-11482.

Azarov I et al. Nitric oxide scavenging by red blood cells as a function of hematocrit and oxygenation. The Journal of Biological Chemistry. Nov. 25, 2005; 280(47): 39024-39032.

Huang KT et al. The reaction between nitrite and deoxyhemoglobin. The Journal of Biological Chemistry. Sep. 2, 2005; 230(35): 31126-31131.

King SB. N-hydroxyurea and acyl nitroso compounds as nitroxyl (HNO) and nitric oxide (NO) donors. Current Topics in Medicinal Chemistry, 2005; 5: 665-673.

Leopold JA and Loscalzo J. Oxidative enzymopathies and vascular disease. Arterioscler Thromb Vasc Biol. 2005; 25: 1332-1340.

Minneci PC et al. Hemolysis-associated endothelial dysfunction mediated by accelerated NO inactivation by decompartmentalized oxyhemoglobin. The Journal of Clinical Investigation. Dec. 2005; 115(12): 3409-3417.

Rother RP et al. The clinical sequelae of intravascular hemolysis and extracellular plasma hemoglobin. JAMA. Apr. 6, 2005; 293(13): 1653-1662.

Jeffers A et al. Computation of plasma hemoglobin nitric oxide scavenging in hemolytic anemias. Free Radic Biol Med. Nov. 15, 2006; 41-(10): 1557-1565.

Kim-Shapiro DB et al. Unraveling the reactions of nitric oxide, nitrite, and hemoglobin in physiology and therapeutics. Arterioscler. Thrmb. Vasc. Biol. 2006; 26: 697-705.

Sha X et al. Hydrolysis of acyloxy nitroso compounds yields nitroxyl (HNO). J. Am. Chem. Soc. 2006; 128: 9687-9692.

Grubina R et al. Concerted nitric oxide formation and release from the simultaneous reactions of nitrite with deoxy- and oxyhemoglobin. Journal of Biological Chemistry. Apr. 27, 2007; 282(17): 12916-12927.

Nitroxyl. Wikipedia. 1 page, printed Aug. 31, 2007.

Product Information: Angeli's Salt. Cayman Chemical. 1 page, printed 2007.

He X et al. The potential of Angeli's salt to decrease nitric oxide scavenging by plasma hemoglobin. Free Radical Biology & Medicine. 2008; 44: 1420-1432.

International Search Report and Written Opinion, PCT/US2008/010950, mailed Dec. 8, 2008.

Paolocci N et al. Nitroxyl anion exerts redox-sensitive positive cardiac inotropy in vivo by calcitonin gene-related peptide signaling. PNAS. Aug. 28, 2001; 98(18): 10463-10468.

Feelisch M. Nitroxyl gets to the heart of the matter. PNAS. Apr. 29, 2003; 100(9): 4978-4980.

Paolocci N et al. Positive inotropic and lusitropic effects of HNO/NO$^-$ in failing hearts: independence from beta-adrenergic signaling. PNAS. Apr. 29, 2003; 100(9): 5537-5542.

Wilson EK. New NO directions: Mesilla workshop highlights increasing evidence that reactive and mysterious HNO may be an important biomolecule. CENEAR. Mar. 8, 2004; 82(10): (10 pp) 39-44.

Miranda KM. The chemistry of nitroxyl (HNO) and implications in biology. Coordination Chemistry Reviews. 2005; 249: 433-455.

Lopez BE et al. The inhibition of glyceraldehyde-3-phosphate dehydrogenase by nitroxyl (HNO). Archives of Biochemistry and Biophysics, 2007: 465: 430-436.

Fukuto JM et al. Nitroxyl (HNO) signaling. Free Radical Biology & Medicine. 2009; 47: 1318-1324.

Yong Q-C et al. Hydrogen sulfide interacts with nitric oxide in the heart: possible involvement of nitroxyl. Cardiovascular Research. 2010; 88: 482-491.

Dumond JF and King SB. The chemistry of nitroxyl-releasing compounds. Antioxidants & Redox Signaling. 2011; 14(9): 1637-1648.

Flores-Santana W et al. The specificity of nitroxyl chemistry is unique among nitrogen oxides in biological systems. Antioxidants & Redox Signaling. 2011; 14(9): 1659-1674.

Fukuto JM and Carrington SJ. HNO signaling mechanisms. Antioxidants & Redox Signaling. 2011; 14(9): 1649-1657.

Tocchetti CG et al. Playing with cardiac "redox switches": the "HNO way" to modulate cardiac function. Antioxidants & Redox Signaling. 2011; 14(9) 1687-1698.

Groves JT and Wang C C-Y. Nitric oxide synthase: models and mechanisms. Current Opinion in Chemical Biology. 2000; 4: 687-695.

The Student Pharmacist (http://thestudentpharmacist.com/?p=570) 2002, The Physicians' Desk Reference, 56$^{th}$ edition, New Jersey, Medical Economics Co., p. 3524.

King SB. N-hydroxyurea and acyl nitroso compounds as nitroxyl (HNO) and nitric oxide (NO) donors. current Topics in Medicinal Chemistry. 2005(7); 5: 665-673.

Huang J et al. Iron nitrosyl hemoglobin formation from the reactions of hemoglobin and hydroxyurea. Biochemistry. 2001; 41(7): 2466-2474.

\* cited by examiner

METHODS OF TREATMENT FOR HEMOLYSIS

RELATED APPLICATIONS

This application is a 35 U.S.C. § §371 national phase application of PCT Application PCT/US2008/010950, filed Sep. 19, 2008, and published in English on Mar. 26, 2009, as International Publication No. WO 2009/038796, and which claims the benefit under 35 U.S.C. § §119(e) of United States Provisional Patent Application Serial Number 60/973,878, filed Sep. 20, 2007, the disclosure of each of which is incorporated herein by reference in its entirety.

STATEMENT OF GOVERNMENT SUPPORT

This work was supported by grant HL58091from the National Institutes of Health. The U.S. Government has certain rights to this invention.

FIELD OF THE INVENTION

This invention concerns methods of treatment for conditions associated with hemolysis.

BACKGROUND OF THE INVENTION

Nitric oxide (NO) bioavailability in the body is important in maintaining several aspects of homeostasis, and its dysfunction contributes to a large variety of diseased states. In endothelial cells, NO is produced by endothelial nitric oxide synthase and can diffuse from the endothelial cells to the smooth muscle cells, where it causes vasodilation via activation of soluble guanylate cyclase (Palmer et al., Nitric-Oxide Release Accounts for the Biological-Activity of Endothelium-Derived Relaxing Factor. *Nature* 327 (6122), 524 (1987)). In the body, nitric oxide is a modulator of, inter alia, vascular permeability (Yuan et al., New insights into eNOS signaling in microvascular permeability. *Am J Physiol Heart Circ Physiol* 291 (3), H1029 (2006)), angiogenesis (Murohara et al., Nitric oxide synthase modulates angiogenesis in response to tissue ischemia. *The Journal of clinical investigation* 101 (11), 2567 (1998)), platelet adhesion and aggregation (Loscalzo, Nitric oxide insufficiency, platelet activation, and arterial thrombosis. *Circulation research* 88 (8), 756 (2001)), and leukocyte adhesion (Kubes et al., Nitric oxide: an endogenous modulator of leukocyte adhesion. *Proceedings of the National Academy of Sciences of the United States of America* 88 (11), 4651 (1991)).

Nitric oxide activity is rapidly diminished in the presence of hemoglobin (Hb). Hemoglobin (Hb) reacts with NO primarily through the dioxygenation reaction (Scheme 1), in which oxygenated Hb (OxyHb) reacts with NO to form Methemoglobin (MetHb, where the heme is oxidized to $Fe^{III}$) and nitrate ($NO_3^-$). Nitric oxide also binds to a ferrous vacant heme (Scheme 2) of deoxygenated Hb (deoxyHb) to form iron nitrosyl Hb ($Fe^{II}$NO-Hb).

$$HbO_2 + NO \rightarrow MetHb + NO_3^- \quad (1)$$

$$Hb + NO \rightarrow Fe^{II}NO\text{-}Hb \quad (2)$$

These reactions occur at nearly diffusion-limited rates: $5\text{-}8 \times 10^7$ $M^{-1}s^{-1}$ for the dioxygenation reaction, and $3 \times 10^7$ $M^{-1}s^{-1}$ for the NO binding reaction to deoxyHb (Huang et al., Nitric Oxide Red Blood Cell Membrane Permeability at high and low Oxygen Tension. *Nitric Oxide* 16, 209 (2007)). The production of nitrate from the dioxygenation reaction is a dead end with respect to NO bioactivity. In addition, any NO that is slowly released from iron nitrosyl Hb is likely to be scavenged by OxyHb, thereby destroying its activity.

In the vascular tissues, nitric oxide is made in a compartment adjacent to the blood, where there is 10 mM Hb (in heme). This presents a paradox as to how NO can function without being scavenged by the Hb (Lancaster, Simulation of the Diffusion and Reaction of Endogenously Produced Nitric-Oxide. *Proc. Natl. Acad. Sci. USA* 91 (17), 8137 (1994)). Based on kinetic calculations in normal physiology, it is thought that endothelial-derived NO is not scavenged to the extent predicted because red blood cell (RBC) encapsulated Hb in the blood reacts with NO much more slowly than does cell-free Hb (Vaughn et al., Erythrocytes possess an intrinsic barrier to nitric oxide consumption. *J. Biol. Chem.* 275 (4), 2342 (2000)).

Without wishing to be bound by theory, three mechanisms are thought to contribute to reduced NO scavenging by RBCs. First, the rate of the reaction is largely limited by external diffusion of NO to the RBC. Second, NO diffusion is partially blocked by a physical barrier across the RBC membrane. Third, RBC encapsulated Hb is efficiently compartmentalized in the lumen; it does not extravasate into the endothelium and interstitium (Kim-Shapiro et al., Unraveling the Reactions of Nitric Oxide, Nitrite, and Hemoglobin in Physiology and Therapeutics. *Arterioscler Thromb Vasc Biol* 26, 697 (2006)).

All three of these mechanisms break down during hemolysis, in which destruction of the RBCs results in release of Hb into the blood plasma, where it can scavenge NO. Supporting this notion, the increased ability of cell-free Hb to scavenge NO has been attributed to the hypertension, increased systemic and pulmonary vascular resistance, and morbidity and mortality associated with administration of hemoglobin-based oxygen carriers (HBOCs or "blood substitutes") (Doherty et al., Rate of reaction with nitric oxide determines the hypertensive effect of cell-free hemoglobin. *Nature Biotechnology* 16 (7), 672 (1998)).

There is also a host of animal and human data supporting the theory that NO scavenging by cell-free Hb due to intravascular hemolysis contributes to disease. For example, the importance of intravascular hemolysis on NO bioavailability in diseased states including hemolytic anemias such as sickle cell disease and paroxysmal nocturnal hemoglobinuria (PNH), thalassemia intermedia, malaria, thrombotic thrombocytopenic purpura, hemolytic uremic syndrome and cardiopulmonary bypass has been elucidated (Gladwin, M. T., Unraveling the hemolytic subphenotype of sickle cell disease. *Blood* 106 (9), 2925 (2005); Minneci et al., Hemolysis-associated endothelial dysfunction mediated by accelerated NO inactivation by decompartmentalized oxyhemoglobin. *J. Clin. Invest.* 115, 3409 (2005); Rother et al., The clinical sequelae of intravascular hemolysis and extracellular plasma hemoglobin—A novel mechanism of human disease. *Jama-J Am Med Assoc* 293 (13), 1653 (2005)).

It has been shown that hemolysis in cardiopulmonary bypass surgery leads to renal tube injury and other complications (Tanaka et al., Administration of Haptoglobin during Cardiopulmonary bypass surgery. *Trans. Am. Soc. Artif. Intern. Organs* 37, M482 (1991)). Minneci et al. demonstrated that intravascular hemolysis leads to vasoconstriction and impairs renal function in a canine model (Hemolysis-associated endothelial dysfunction mediated by accelerated NO inactivation by decompartmentalized oxyhemoglobin. *J. Clin. Invest.* 115 (12), 3409 (2005)).

Reiter et al. found that responsiveness to NO administration was blunted by 80% in patients with sickle cell anemia who had plasma heme concentrations greater than or equal to 6 μM (Cell-free hemoglobin limits nitric oxide bioavailability in sickle-cell disease. *Nat. Med.* 8 (12), 1383 (2002)). The hemolysis in sickle cell disease is generally lower than that of other conditions, with an average of 4.2±1.1 μM during steady state, compared to 0.2±0.1 μM for control normal volunteers. However, hemolysis increases several fold during sickle cell crisis (Naumann et al., Plasma hemoglobin and hemoglobin fractions in sickle cell crisis. *Am. J. Clin. Pathol.* 56, 137 (1971); Ballas et al., Hyperhemolysis during the evolution of uncomplicated acute painful episodes in patients with sickle cell anemia. *Transfusion* 46 (1), 105 (2006)).

We have conducted calculations demonstrating that only 1 μM cell-free Hb significantly reduces NO bioavailability, even in the background of the 10 mM or so Hb (in heme) found in whole blood (Jeffers et al., Computation of plasma hemoglobin nitric oxide scavenging in hemolytic anemias. *Free Radic. Biol. Med.* 41 (10), 1557 (2006)). Thus, pathology associated with low NO bioavailability is an important contributor to pathology in conditions involving hemolysis.

Reiter et al. showed that NO inhalation therapy can result in conversion of plasma OxyHb to MetHb in patients with sickle cell disease, thereby reducing the enhanced NO scavenging of the plasma Hb (Cell-free hemoglobin limits nitric oxide bioavailability in sickle-cell disease. *Nat. Med.* 8 (12), 1383 (2002)). Similarly, in the canine model, Minneci et al. showed that NO inhalation following hemolysis resulted in restoration of NO responsiveness to NO donors and attenuation of the hemolysis-associated vasoconstriction (Hemolysis-associated endothelial dysfunction mediated by accelerated NO inactivation by decompartmentalized oxyhemoglobin. *J. Clin. Invest.* 115 (12), 3409 (2005)). These results support the approach of oxidizing the cell-free Hb to diminish NO scavenging. Indeed, NO inhalation therapy in sickle cell disease and other hemolytic conditions has been gaining increased attention.

Although use of NO inhalation therapy holds promise for treatment of hemolytic conditions, its use is not practical in a variety of settings, particularly where chronic treatment is desired. NO inhalation therapy is expensive, and compliance in its use with portable gas cylinders is not likely to be great. In addition, formation of MetHb as an end-product during NO therapy may not be ideal due to potential oxidative damage (Alayash, Oxygen therapeutics: Can we tame haemoglobin? *Nat Rev Drug Discov* 3 (2), 152 (2004); Motterlini et al., Oxidative-Stress Response in Vascular Endothelial-Cells Exposed to Acellular Hemoglobin-Solutions. *Am. J Physiol.-Heart Circul. Physiol.* 38 (2), H648 (1995); Balla et al., Endothelial-Cell Heme Uptake from Heme-Proteins—Induction of Sensitization and Desensitization to Oxidant Damage. *Proc. Natl. Acad. Sci. USA* 90 (20), 9285 (1993)).

Therefore, new approaches are needed in the treatment of conditions associated with hemolysis.

SUMMARY OF THE INVENTION

Provided herein are methods of treating hemolysis (e.g., intravascular hemolysis) in a subject in need thereof, comprising: administering an active compound to said subject in an amount sufficient to treat said hemolysis. In some embodiments the active compound:

a) preferentially reacts with cell-free OxyHb, as compared to OxyHb encapsulated in a red blood cell; and b) reacts with MetHb to form iron-nitrosyl Hb or nitrite bound MetHb.

In some embodiments, the active compound results in a reduction of the total amount of cell-free Hb in blood plasma.

In some embodiments, the active compound results in a reduction of hemolysis. In some embodiments, the active compound comprises a nitroxyl donor (e.g., Angeli's salt).

In some embodiments, the methods further comprise administering to said subject: (i) red blood cells and/or (ii) an agent that promotes hematopoiesis.

Also provided are methods of treating hemolysis in a subject in need thereof comprising: administering an active compound to said subject in an amount sufficient to treat said hemolysis, while concurrently administering a nitric oxide donor (e.g., NONOate).

Further provided is the use of an active compound as described herein to treat hemolysis in a subject in need thereof.

BRIEF DESCRIPTION OF THE DRAWINGS

FIG. 9. AS reduces hemolysis. The common marker for hemolysis, Lactate Dehydrogenase (LDH), was measured for each animal during the AS infusions. The rise in LDH is substantially more apparent in animals not receiving AS.

DETAILED DESCRIPTION OF THE PREFERRED EMBODIMENTS

Figure 1A:
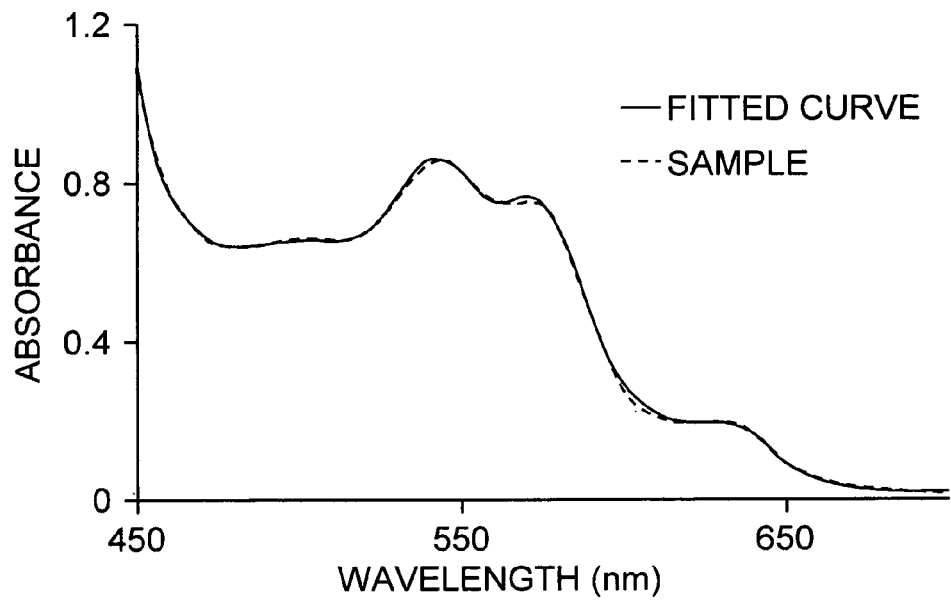
FIG. 1. Spectral deconvolution of Hb species absorption. 1A: Typical fit of an absorption spectrum showing both the raw data and the fit. $Fe^{II}NO$-Hb found was 29%, the percentage of OxyHb was 4.9%, deoxyHb was 21%, the percentage of MetHb was 41%, and MetHb-$NO_2^-$ was 4%. 1B: The basis spectra used for fitting.

The present invention is explained in greater detail in the non-limiting embodiments described further below. The disclosures of all United States patent references cited herein are hereby incorporated by reference to the extent they are consistent with the disclosure set forth herein.

As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

"Hemolysis" (e.g., intravascular hemolysis) as used herein is the breaking open of red blood cells (RBCs, red cells) and the release of the red blood cell encapsulated hemoglobin (Hb) into the surrounding fluid ("cell-free" Hb). Hemolysis can occur in blood vessels ("intravascular hemolysis") or in other parts of the body ("extravascular hemolysis").

The normal life span of red blood cells in the body is approximately 120 days, amounting to about 1% of RBCs breaking down each day. Multiple systems have evolved to process and control the level of cell-free Hb in the plasma during this normal physiological breakdown of RBCs (see Rother et al., The clinical sequalae of intravascular hemolysis and extracellular plasma hemoglobin, JAMA 293(13):1563-1662 (2005)). However, during hemolysis, cell-free Hb may overwhelm these systems and lead to NO scavenging by the cell-free Hb.

We have determined that 1 μM cell-free Hb significantly reduces NO bioavailability, even in the background of the 10 mM or so Hb (in heme) found in whole blood (Jeffers et al., Computation of plasma hemoglobin nitric oxide scavenging in hemolytic anemias. *Free Radic. Biol. Med.* 41 (10), 1557 (2006)). Therefore, in some embodiments hemolysis is treated when cell-free Hb is greater than 0.1, 0.5 or 1 μM, or between 0.1 μm and 50 mM, etc.

There is about 10 mM Hb in heme, and 1% of 10 mM is 100 μM. In steady state sickle cell disease, one typically has 4 uM cell-free Hb. Our studies have indicated that 1 μM cell-free Hb (0.01%) affects NO bioavailability. Therefore, in some embodiments hemolysis is defined as a percentage of cell-free Hb (cell-free Hb/total Hb) exceeding about 0.01% (e.g., greater than 0.005%, 0.01%, 1% %, etc.) In further embodiments, hemolysis is defined as a percentage of cell-free Hb (cell-free Hb/total Hb) exceeding about 1% (e.g., greater than 0.5%, 1.0%, 2.0%, etc.).

Hemolysis can be diagnosed according to methods known to those of skill in the art. For example, abnormalities of RBC morphology, increased levels of serum LDH, etc. may be suggestive of hemolysis, and these and other tests generally known in the medical community may be used for a diagnosis of hemolysis. Visually, hemolysis may be seen as a pink to red tinge in serum or plasma. Hemolysis may also be identified by directly measuring RBC survival with a radioactive label (e.g., $^{51}$Cr).

One effect of hemolysis is a decrease in NO bioavailability due to Hb scavenging of the plasma NO, as described above. Clinical consequences of excessive cell-free plasma Hb include dystonias involving gastrointestinal, cardiovascular, pulmonary and urogenital systems, clotting disorders, etc. (see Rother et al., "The clinical sequelae of intravascular hemolysis and extracellular plasma hemoglobin," JAMA 293 (13):1653-1662 (2005)).

Intravascular hemolysis is associated with many diseases, conditions and procedures (see Rother et al., The clinical sequelae of intravascular hemolysis and extracellular plasma hemoglobin, JAMA 293(13):1653-1662 (2005)). For example, microangiopathic hemolytic anemias (e.g., thrombotic thrombocytopenic purpura, TTP, hemolytic uremic syndrome, HUS) and enzymopathies (e.g., pyruvate kinase defiency), paroxysmal nocturnal hemoglobinuria, sickle cell (e.g., in sickle cell crisis), thalassemia, red cell membrane disorders, red cell enzymopathies, thrombotic thrombocytopenic purpura, malaria, cardiopulmonary bypass, transfusion of aged blood, alloimmune hemolysis, etc., all typically involve intravascular hemolysis.

Hemolysis can lead to "hemolytic anemia" when bone marrow production of new red blood cells cannot compensate for the shortened red blood cell life span. Hemolytic anemia can be acquired (e.g., infection or certain medications) or inherited (e.g., sickle-cell anemia). Types of hemolytic anemia include, but are not limited to, microangiopathic hemolytic anemias (e.g., thrombotic thrombocytopenic purpura, TTP, hemolytic uremic syndrome, HUS), sickle-cell anemia, paroxysmal nocturnal hemoglobinuria, hemoglobin SC disease, hemolytic anemia due to G6PD deficiency, hereditary elliptocytosis, hereditary spherocytosis, hereditary ovalocytosis, idiopathic autoimmune hemolytic anemia, non-immune hemolytic anemia caused by chemical or physical agents, secondary immune hemolytic anemia, thalassemia, etc. Severe hemolytic anemia can cause cardiovascular collapse.

Hemolysis can also occur during surgical procedures (e.g., cardiopulmonary bypass), where blood is salvaged from the patient and returned to circulation. Further, hemolysis can occur upon the administration of certain drugs, e.g., penicillin, primaquine, dapsone, sulfasalazine, ouabaine, etc. It also can result from jellyfish stings, snake bites, and poisoning.

A consequence of hemolysis is the scavenging of nitric oxide (NO) by the cell-free hemoglobin, which can lead to hypertension, increased systemic and pulmonary vascular resistance, and morbidity and mortality (e.g., as associated with the administration of hemoglobin-based oxygen carriers (HBOCs or "blood substitutes")). During intravascular hemolysis, vasomotor tone and organ perfusion may be impaired (e.g., impaired renal function) by the increased reactivity of cell-free plasma hemoglobin with nitric oxide.

"Hemoglobin" or "Hb" is a oxygen-transporting metalloprotein with iron-containing heme groups, and is typically found in the red blood cells of the blood in humans and other animals. In humans, hemoglobin is a tetramer of two a subunits and two β subunits. Each subunit contains one heme, and each of the two β subunits also contain reactive cysteines (β-cys93). Mutations in the hemoglobin gene may result in hereditary diseases called hemoglobinopathies (e.g., sickle cell disease).

"OxyHb" is oxygen-bound hemoglobin. Oxygen is normally transferred to Hb in the pulmonary capillaries adjacent to the alveoli of the lungs, and is transported by the OxyHb in the red blood cells to other parts of the body.

"Methemoglobin" or "MetHb" is the oxidized form of hemoglobin, in which the iron in the heme component has been oxidized from the ferrous (+2) to the ferric (+3) state. This renders the hemoglobin molecule incapable of effectively transporting and releasing oxygen to the tissues. Methemoglobinemia is a condition in which a substantial portion of the hemoglobin in the blood of a subject is in the form of MetHb. See, e.g., U.S. Patent Application Publication No. 2007/0154569 to Gladwin et al., which is incorporated by reference herein.

The formation of MetHb as an end-product (e.g., of the NO reaction with cell-free Hb) may promote oxidative damage in the body. Therefore, in some embodiments "active compounds" of the present invention are those compounds that convert OxyHb to MetHb and further convert MetHb to iron nitrosyl Hb or other stable forms such as nitrite bound MetHb (MetHb-$NO_2^-$). Examples of active compounds disclosed herein include nitroxyl donors. For example, in some embodiments, at least 1%, 2, 5, or 10% of the MetHb has nitrite bound to it after administration of an effective amount of an active compound described herein for approximately 1, 2 or 3 hours.

"Nitric oxide" (NO) is a natural vasodilator generated from L-arginine by NO synthase. A "nitric oxide donor" is an agent that directly promotes the availability of NO by releasing NO under physiological conditions. See, e.g., U.S. Pat. No. 5,958,427 to Salzman et al. and U.S. Pat. No. 5,994,444 to Trescony et al.

"Nitrite" ($NO_2^-$) is the inorganic anion or a salt of nitrous acid ($HNO_2$). The administration of nitrite to a subject causes vasodilation. See U.S. Patent Application Publication No. 2007/0154569 to Gladwin et al.

"Nitroxyl" (HNO/$NO^-$, nitrosyl hydride/nitroxyl anion) or hyponitrous acid, is the reduced form of nitric oxide (NO). HNO and $NO^-$ form an acid/base pair, with $NO^-$ isoelectronic with dioxygen. Because of its reactive nature, nitroxyls are often prepared in situ with the use of nitroxyl donors.

In general, nitroxyl (HNO/$NO^-$) and nitric oxide (NO) have different reactivities and exhibit distinct biological effects in the body (see Miranda et al., A biochemical rationale for the discrete behavior of nitroxyl and nitric oxide in the cardiovascular system, Proc. Natl. Acad. Sci. 100(16): 9196-9210 (2003); Miranda et al., Comparison of the reactivity of nitric oxide and nitroxyl with heme proteins: A chemical discussion of the differential biological effects of these redox related products of NOS, J. Inorg. Biochem. 93:52-60 (2002)). For instance, administration of Angeli's salt, a nitroxyl donor, increases myocardial performance without altering heart rate, while NO donor administration causes vasodilatation accompanied by an increase in heart rate.

A "nitroxyl donor" is an agent or compound that provides a physiologically effective amount of nitroxyl (HNO and/or NO (HNO/$NO^-$)). Examples of nitroxyl donating compounds include, but are not limited to, Angeli's salt ($Na_2N_2O_3$), isopropylamine diazeniumdiolate, Piloty's acid ($PhSO_2NHOH$), and similar compounds (see, e.g., U.S. Pat. No. 6,936,639 to Wink et al.; U.S. Patent Application Publication No. 20070191377).

In preferred embodiments, an "effective" nitroxyl donor in treating hemolysis is one that leads to preferential reactivity with cell-free hemoglobin as opposed to that encapsulated in the red blood cell.

"Preferential reactivity" as used herein is when there is at least 2-, 3- or 5-fold higher, or more, percentage of reactivity with hemoglobin (reacted hemoglobin/unreacted hemoglobin) that is cell-free compared to that in the RBC. This can be measured using techniques known in the art (Azarov et al., Nitric oxide scavenging by red blood cells as a function of hematocrit and oxygenation. *J. Biol. Chem.* 280 (47), 39024 (2005) or Huang et al., Nitric Oxide Red Blood Cell Membrane Permeability at high and low Oxygen Tension. *Nitric Oxide* 16, 209 (2007)) and described herein.

"Angeli's salt" or "AS" ($Na_2(ONNO_2)$) is a preferred nitroxyl donor. As a crystalline salt, AS may be stored at −20 degrees Celsius for six months or more. AS dissociates in a pH-dependent manner following first-order kinetics, releasing 0.54 moles of $NO^-$ per mole of parent compound. Alkaline solutions (e.g., 0.01 M NaOH) are relatively stable and can typically be stored at 0 degrees Celsius for 24 hours. The half-life of AS in 0.1 M phosphate buffer, pH 7.4, is approximately 2.3 minutes at 37 degrees Celsius.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric.

Subjects may also include animal subjects, particularly mammalian subjects such as canines, felines, bovines, caprines, equines, ovines, porcines, rodents (e.g., rats and mice), lagomorphs, non-human primates, etc., for, e.g., laboratory testing, veterinary medicine and/or pharmaceutical drug development purposes.

"Treat" refers to any type of treatment that imparts a benefit to a patient, e.g., a patient afflicted with or at risk for developing a disease or condition (e.g., a disease associated with hemolysis). Treating includes actions taken and actions refrained from being taken for the purpose of improving the condition of the patient (e.g., the relief of one or more symptoms), delay in the onset or progression of a disease or condition, lessening of one or more symptoms associated with hemolysis, etc. In some embodiments, treating hemolysis includes the administration of an active compound (e.g., a nitroxyl donor) to a subject in need thereof. In some embodiments, treating hemolysis further includes the administration of blood and/or a blood substitute, an agent that promotes hematopoiesis, steroid therapy (e.g., in immune-related hemolytic anemia), NO therapy, etc. This may be accomplished by, e.g., the combination therapies described below.

The administration of two or more compounds "in combination" means that the two compounds are administered closely enough in time to have an additive and/or synergistic effect. The two compounds may be administered simultaneously (concurrently) or sequentially. Simultaneous administration may be carried out by mixing the compounds prior to administration, or by administering the compounds at the same point in time but at different anatomic sites or using different routes of administration.

The phrases "concurrent administration" and "administration in combination" mean that the compounds are administered at the same point in time or immediately following one another. In some embodiments, the two compounds are administered "simultaneously," i.e., at times sufficiently close that the results observed are indistinguishable from those achieved when the compounds are administered at the same point in time.

"Pharmaceutically acceptable" as used herein means that the compound or composition is suitable for administration to a subject to achieve the treatments described herein, without unduly deleterious side effects in light of the severity of the disease and necessity of the treatment.

"Prodrug" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound or active agent, for example, by hydrolysis in blood.

1. Active Compounds.

Active compounds of the present invention constitute those that convert OxyHb to MetHb and further convert MetHb to iron nitrosyl Hb or other stable forms which are not especially redox active such as nitrite bound MetHb. Examples of active compounds include nitroxyl donors such as Angeli's salt (AS).

It is demonstrated herein that AS can be used to preferentially convert cell-free OxyHb to MetHb in the presence of excess, physiologically relevant concentrations of RBC-encapsulated Hb. In addition, AS also forms potentially less redox active end-products including iron nitrosyl Hb and nitrite bound MetHb. Thus, Angeli's salt or a similar compound (e.g., a nitroxyl donor) could be used to effectively treat hemolysis by attenuating the NO scavenging of the Hb released by ruptured RBCs.

First, AS is efficient at converting OxyHb to MetHb, and a significant portion of this has nitrite bound (e.g., at least 1%, 2%, 3%, 4%, 5% or 6%, or between 1%, 2%, 3%, 4%, 5%, or 6% and 10%, 15%, 20%, 40%, or 50% or more, measured, e.g., 1, 2, or 3 hours after administration). Angeli's salt decomposes into nitrite ($NO_2^-$) and nitroxyl ($HNO/NO^-$), and the nitroxyl reacts with OxyHb to make MetHb:

$$HN_2O_3^- \rightarrow NO_2^- + HNO \qquad (3)$$

$$HNO + 2\ OxyHb \rightarrow +2\ MetHb. \qquad (4)$$

Second, we have found that AS will further convert MetHb to $Fe^{II}NO$-Hb, which is a more stable form (see FIG. 5). As mentioned above, the formation of MetHb as an end-product may not be ideal due to potential oxidative damage. Therefore, the conversion of MetHb to the more stable $Fe^{II}NO$-Hb by active compounds described herein is beneficial. As the products of these reactions described above do not effectively scavenge NO, AS and other active compounds (e.g., nitroxyl donors) described herein are useful to treat hemolysis and restore NO availability.

Third, AS preferentially reacts with cell-free Hb compared to RBC encapsulated Hb. The reaction of HNO with OxyHb has been found to be extremely fast (about $10^7\ M^{-1}s^{-1}$) (Miranda et al., A biochemical rationale for the discrete behavior of nitroxyl and nitric oxide in the cardiovascular system. *Proc. Natl. Acad. Sci. USA* 100 (16), 9196 (2003)). Thus, nitroxyl preferentially reacts with cell-free Hb compared to RBC encapsulated Hb in a similar way as NO. Furthermore, the preferential reactivity is greatest at low hematocrit, as occurs in hemolytic anemias (hematocrit is the proportion of blood volume occupied by red blood cells).

In addition, and without wishing to be bound by theory, due to the fact that RBCs travel fastest in the middle of blood vessels, a pressure gradient is formed, which pushes the RBCs inward, creating a RBC-free zone near the endothelium (Butler et al., Diffusion of nitric oxide and scavenging by blood in the vasculature. *Biochim. Biophys. Acta* 1425 (1), 168 (1998)). In this zone, AS will only react with cell-free Hb, which is not pushed to the center of the vessel with the RBCs. This effect causes an even higher preference of AS to react with cell-free Hb.

Furthermore, in some embodiments, administration of an effective amount of an active compound reduces the total amount of cell-free Hb in blood plasma. In some embodiments, administration of an effective amount of an active compound reduces the amount and/or rate of hemolysis.

2. Pharmaceutical Formulations.

The active compounds described above may be formulated for administration in a pharmaceutical carrier in accordance with known techniques. See, e.g., Remington, *The Science And Practice of Pharmacy* (9th Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

For example, in some embodiments active compounds are administered intravenously for cardiopulmonary bypass, sickle cell crisis, and other acute treatment which may require hospitalization. In some embodiments active compounds are administered transdermally for jellyfish stings. In some embodiments, active compounds are administered orally for chronic treatments.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy that includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound as described herein, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.001, 0.01 or 0.1 to about 50 mg/kg may be used, with all weights being calculated based upon the weight of the active compound, including the cases where a salt is employed. The frequency and duration of the treatment depends upon the underlying condition being treated. In some embodiments treatment can be once or twice per day for a period of two to four months or more, or until the condition is essentially controlled.

In some embodiments, active compounds may be administered at a dose of between 0.5, 1, 5, or 10 and 20, 25, 50 or 100 µg/kg/min. In some embodiment the infusion is from 1, 2, or 5 minutes to 10, 100, 300 or 600 minutes. As an example, active compounds may be administered at a dose of 15 µg/kg/min for 6 hours (360 minutes).

In some embodiments, the dosage may be calculated so that the total molar concentration of the active compound administered after some time (e.g., from 1, 2, or 5 minutes to 10, 100, 300 or 600 minutes) is equal to or greater than some significant fraction (e.g., ¼, ½, ¾, etc.) of the molar concentration of cell-free Hb. In further embodiments, the dosage may be calculated to be equimolar to the concentration of cell-free Hb, 1.5 time the molar concentration, or twice the molar concentration.

4. Combination Therapies.

Hemolysis results in the release of hemoglobin into the surrounding tissue, which can scavenge free NO, causing, e.g., vasoconstriction. Hemolysis can also result in anemia when the production of red blood cells in the body cannot compensate for the premature destruction of red blood cells.

Therefore, in some embodiments combination therapies for hemolysis include agents that promote the availability of nitric oxide, directly or indirectly (e.g., a NONOate such as spermine NONOate). See, e.g., U.S. Patent Application Publication No. 20060009431 (Earl et al.). In further embodiments, active compounds of the present invention are administered in combination with L-arginine or L-citrulline. See, e.g., U.S. Pat. No. 6,028,107 to Waugh. In further embodiments, active compounds are administered in combination with NO gas. See, e.g., U.S. Pat. No. 5,885,621 to Head et al.

In other embodiments, active compounds are administered in combination with non-ionic surfactants to prevent hemolysis. See, e.g., U.S. Pat. No. 5,880,123 to Harrison.

In some embodiments combination therapies for hemolysis include agents that increase hematocrit (i.e., proportion of blood volume occupied by red blood cells), e.g., compositions comprising red blood cells or promoters of erythropoiesis. Promoters of erythropoiesis include, but are not limited to, erythropoietin, T-4 immune stimulating factor (U.S. Pat. No. 7,196,060 to Beardsley et al.), derivatives of human chorionic gonadotropin (U.S. Pat. No. 5,968,513), etc.

Some embodiments of the present invention are explained in greater detail in the following non-limiting Examples.

EXAMPLE 1

Preferential Reactivity of Angeli's Salt with Cell-Free Hb and Formation of a more Stable Form of Hb Angeli's salt (AS) was purchased from Cayman Chemical (Ann Arbor, Mich.). All other chemicals were obtained from Sigma Chemical Company (St. Louis, Mo.). Blood was obtained from volunteers or bought from the Interstate Blood Bank (Memphis, Tenn.). RBCs were obtained by washing the blood three times in pH 7.4 phosphate buffered saline (PBS). Hb was purified as described previously (Huang et al., Nitric oxide binding to oxygenated hemoglobin under physiological conditions. *Biochim. Biophys. Acta* 1568 (3), 252 (2001); Geraci et al., Preparation and properties of α- and β-chains from human hemoglobin. *J. Biol. Chem.* 17, 4664 (1969)). The washed red blood cells were lysed by incubation with distilled water and the membranes spun out by centrifugation. After extensive dialysis against distilled water, the Hb was pelleted in liquid nitrogen and stored at −80° C.

MetHb was prepared by incubation with excess ferricyanide, and the excess ferricyanide was removed by column filtration (G-25) and dialysis. DeoxyHb was prepared by diluting Hb into deoxygenated PBS buffer obtained by bubbling the buffer with nitrogen or argon in a septum capped flask with an exit needle also present. The Hb was further deoxygenated by purging the solution with argon or nitrogen in a septum capped flask (without inserting the purge needle into the solution).

Absorption spectroscopy on Hb was performed using a Cary 50 Bio Spectrometer in the visible wavelength range (Varian Inc., Walnut Creek, Calif.). Absorption spectroscopy of blood or RBCs was measured in the visible or near infra red range using a PerkinElmer Life Sciences Lambda 9 spectrometer (PerkinElmer Life and Analytical Sciences, Inc., Waltham, Mass.) equipped with an integrating sphere to detect scattered light. Septum capped cells were used for experiments performed in other than ambient atmospheric conditions.

Electron paramagnetic resonance (EPR) spectroscopy was performed using a Bruker EMX 10/12 spectrometer (Bruker Optics Inc., Billerica, Mass.) cooled using liquid helium and operating at 9.4 GHz. Iron nitrosyl Hb was detected at 110 K using 5-G modulation, 10.1-milliwatt power, 655.36-ms time constant, and 167.77-s scan or 327.68-ms time constant and 83.89-s scans over 600 G. 5-G modulation, 10.1-milliwatt power, 655.36-ms time constant, and 167.77-s scan or 327.68-ms time constant and 83.89-s scan over 600 G at 110 K. The concentration of each species was determined by performing a double integral of the EPR spectrum and comparing to standard samples.

Figure 1B:
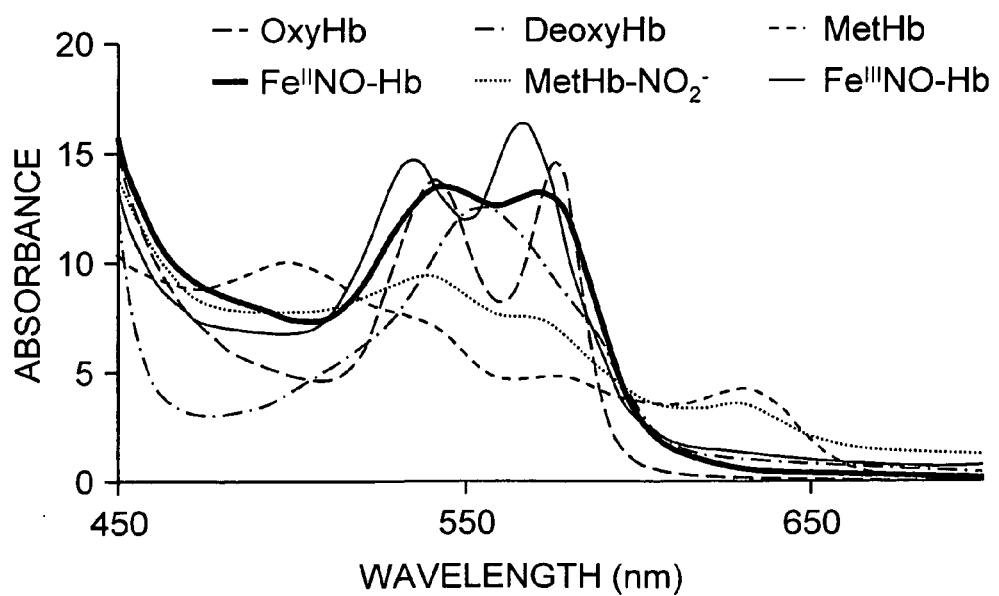

Time resolved absorption spectroscopy was performed by mixing reactive species (Hb and AS) and taking absorption spectra at defined time intervals. Concentrations of known species were obtained by performing a least squares fit to known basis spectra of each species (FIG. 1). In most cases spectral data were fit to all the species shown in FIG. 1B, with the exception being NO bound to MetHb ($Fe^{III}$NO-Hb) since this species is not expected to accumulate to a measurable amount. To insure Fe$^{III}$NO-Hb was not present, it was occasionally included in the fit parameters and always found not to be present at significant quantities or to improve the residuals significantly. Data presented on the percentage of each species includes those species that were present at greater than 1% according to the fits.

Preferential reactivity of AS with cell-free Hb compared to that encapsulated in red blood cells was performed based on Vaughn et al. (Erythrocytes possess an intrinsic barrier to nitric oxide consumption. *J. Biol. Chem.* 275 (4), 2342 (2000)) and modified as described in detail previously (Liu et al., Diffusion-limited reaction of free nitric oxide with erythrocytes. *J. Biol. Chem.* 273 (30), 18709 (1998)). Briefly, AS (50 µM) was added to a mixture of Hb at a final concentration of and RBCs at a hematocrit (Hct) comparable to that found in normal physiology (45%) or comparable to that of patients during sickle cell crisis (18%) (see Ballas, S. K. and Marcolina, M. J., Hyperhemolysis during the evolution of uncomplicated acute painful episodes in patients with sickle cell anemia. *Transfusion* 46 (1), 105 (2006)). The RBCs were spun down and three samples were loaded into EPR tubes and frozen for analysis: (1) one containing a sample from the supernatant used to determine the amount of reacted cell-free Hb, (2) another from the pellet used to determine the amount of reacted RBC encapsulated Hb, and (3) one from the sample before centrifugation to determine the total amount of reacted Hb that should be equal to that in the other two EPR tubes. The preferential reactivity, $k_f/k_r$, of AS is defined by the ratio of the bimolecular rate constant for the reaction of AS with cell-free Hb ($k_f$) to that of the reaction of AS with RBC encapsulated Hb ($k_r$). The preferential reactivity is calculated from the relation $$\frac{[MetHb]_f}{[MetHb]_r} = \frac{k_f [HbO_2]_f}{k_r [HbO_2]_r}, \quad (5)$$

where the subscripts r and f refer to the RBC encapsulated and cell-free Hb respectively. This equation states that the amount of MetHb made in the red cell or cell-free fraction depends on the intrinsic, bimolecular (normalized by the concentration of Hb) rate constant and the amount of reacting material in each fraction. The concentrations (indicated by brackets) represent the moles of the species in the total volume. Thus, $$[MetHb]_f = (1-Hct)*[MetHb]_s, \quad (6)$$

where $[MetHb]_s$ represents the concentration of MetHb in the supernatant. A similar equation is used to determine $[HbO_2]_f$ from the concentration of OxyHb in the supernatant ($[HbO_2]_f = (1-Hct)*[HbO_2]_s$ where the subscript "s" refers to the supernatant). For partially deoxygenated samples, where the products included both Fe$^{II}$NO-Hb and MetHb, the sum of these products in each fraction was used to determine $k_f/k_r$. Since the concentration of cell-free Hb is not constant during the reaction, when necessary, a term accounting for this was included when calculating, $k_f/k_r$ as described previously (Vaughn et al., Erythrocytes possess an intrinsic barrier to nitric oxide consumption. *J. Biol. Chem.* 275 (4), 2342 (2000)).

A self-consistency check was imposed on the data, whereby if the sum of the reacted Hb in the supernatant plus that in the red cells was significantly different from that in the whole mixture (leading to calculated values of $k_f/k_r$ that differ by over 30%), the data were discarded (Azarov et al., Nitric oxide scavenging by red blood cells as a function of hematocrit and oxygenation. *J. Biol. Chem.* 280 (47), 39024 (2005)).

Figure 2A:
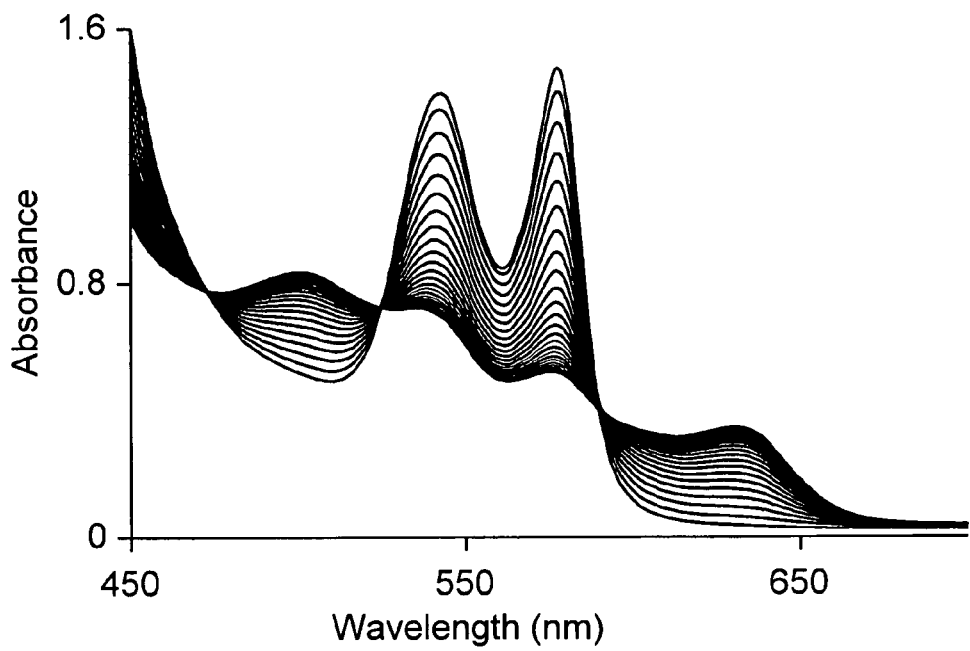
FIG. 2. The reaction of Angeli's salt with a molar excess of OxyHb. OxyHb (100 μM) was mixed with 50 μM Angeli's salt in 0.1 M phosphate buffer under aerobic conditions. 2A: UV-Vis spectra were recorded at 3.0 min intervals after the initial scan. 2B: Each spectrum was fit to basis spectra to determine the percentage of each species at each time point. 2C: The average amount of each species formed at 72 minutes from three different experiments. Standard deviations are also shown.
Figure 2B:
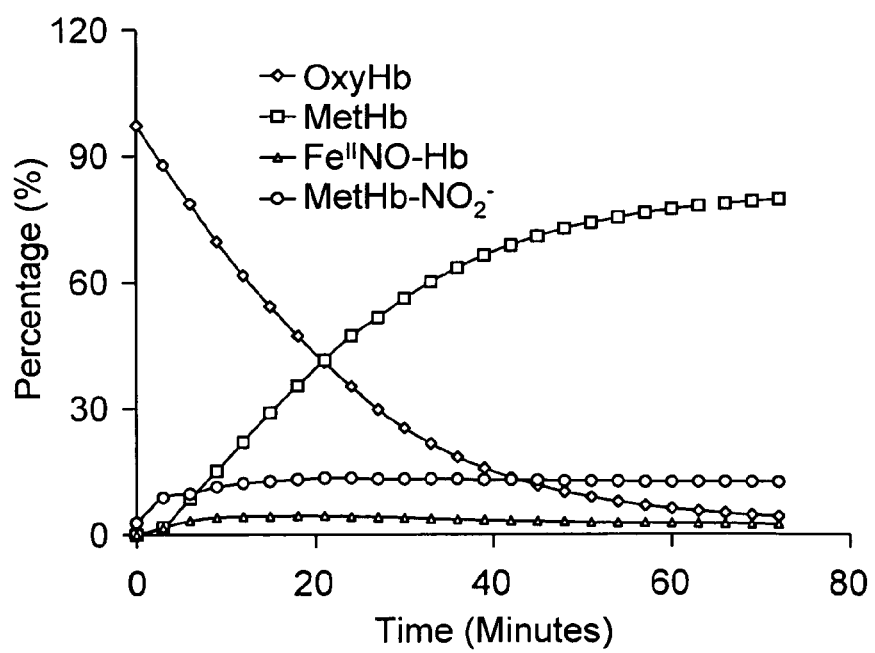

Results: According to Scheme 4, we expect one mole of HNO to convert two moles of OxyHb to two moles of MetHb. Consistent with previous reports (Doyle et al., Oxidation and Reduction of Hemoproteins by Trioxodinitrate(Ii)—the Role of Nitrosyl Hydride and Nitrite. *J Am Chem Soc* 110 (2), 593 (1988)), this is confirmed when we mixed 50 µM of AS with 100 µM of OxyHb (FIG. 2). FIG. 2A shows representative time-resolved absorption spectra from a single experiment and FIG. 2B shows the results from deconvoluting these spectra into their components. The reaction (which is rate-limited by the conversion of AS to HNO and nitrite) is essentially over after seventy minutes. At the final time point, it was measured that 92% of the Hb is MetHb and we also observed that about 16% of this has nitrite bound.

Figure 2C:
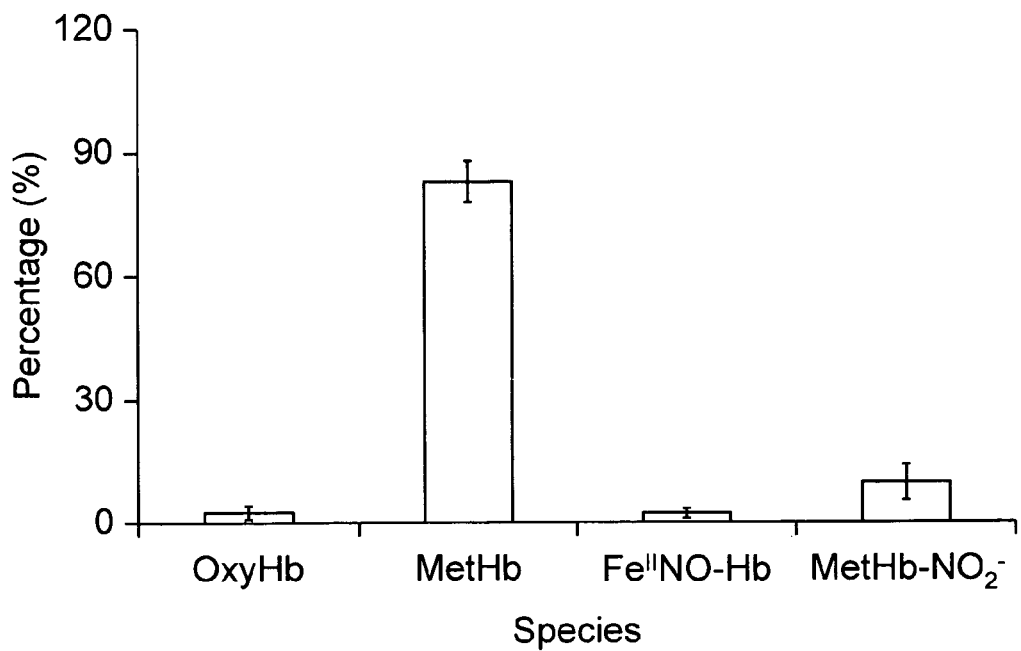

FIG. 2C shows the average relative concentration of species at 72 minutes from three separate experiments. Very little Fe$^{II}$NO-Hb is made under these conditions. It is possible that some of the OxyHb was converted to MetHb via a direct reaction with nitrite. However, given the slow kinetics of the nitrite/OxyHb reaction (Doyle et al., Involvement of Peroxide and Superoxide in the Oxidation of Hemoglobin by Nitrite. *Biochem. Biophys. Res. Commun.* 105 (1), 127 (1982)), this reaction is not expected to be important. We confirmed this by mixing 100 µM of nitrite with 100 µM of OxyHb for 72 minutes and we found that only 2.4 µM of MetHb was formed (data not shown).

Figure 3A:
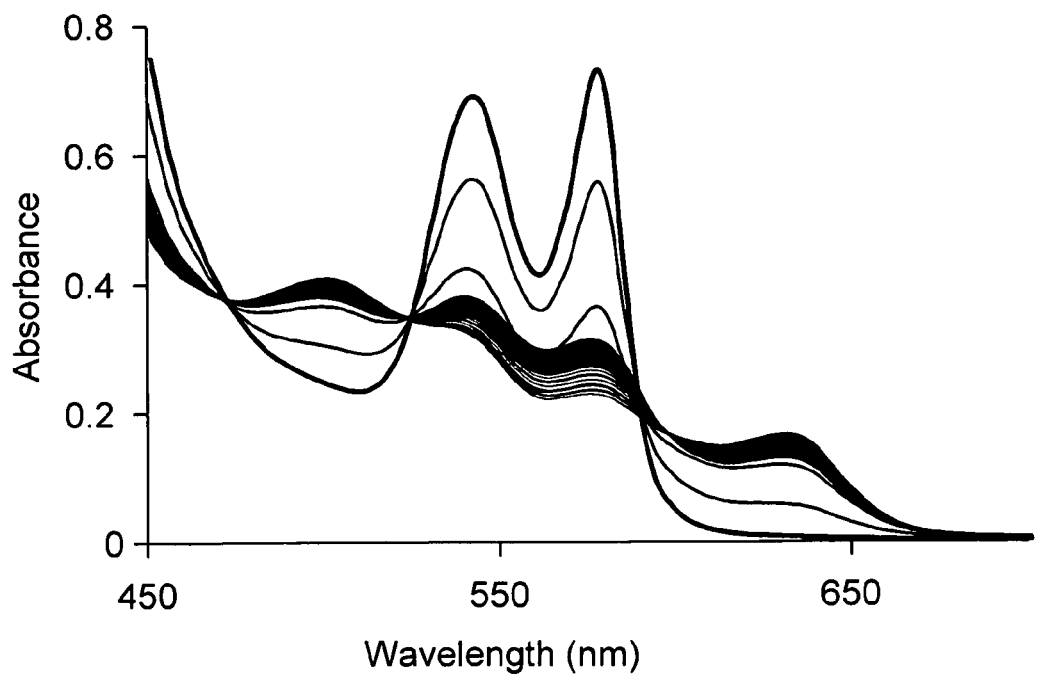
FIG. 3. The reaction of Angeli's salt with equi-molar OxyHb. OxyHb (100 μM) was mixed with 100 μM Angeli's salt in 0.1 M phosphated buffer under aerobic conditions. 3A: UV-Vis spectra were recorded at 3.0 min intervals after the initial scan. 3B: Each spectrum was fit to basis spectra to determine the percentage of each species at each time point.
Figure 3B:
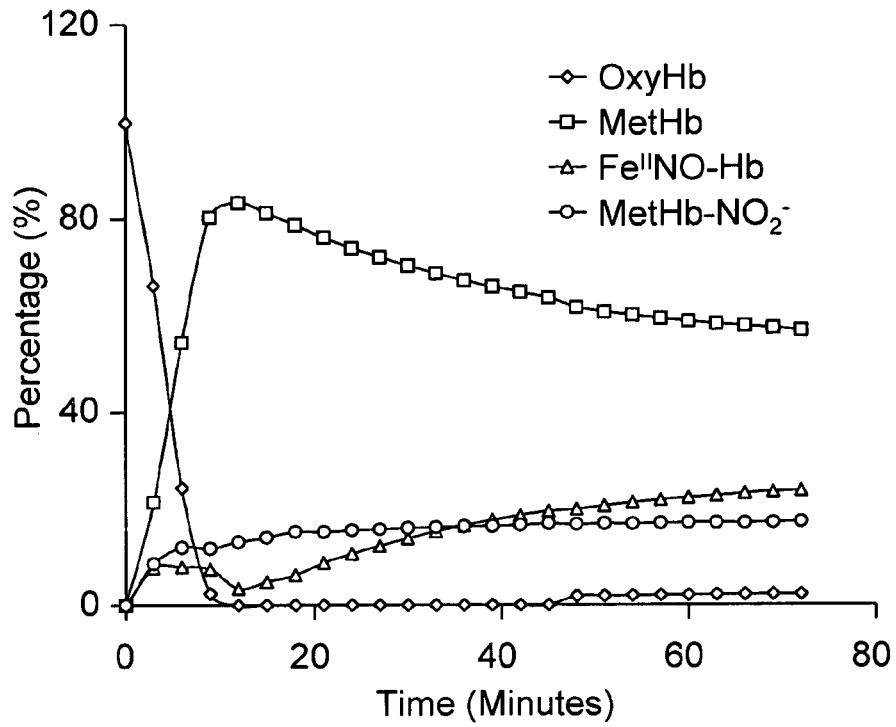

FIG. 3 shows the results from mixing equimolar amounts (100µM) of AS and OxyHb. FIG. 3A shows representative spectra and FIG. 3B shows the results from deconvolution into basis spectra. Here, the OxyHb is essentially gone within 10 minutes, forming mostly MetHb with some bound to nitrite and also forming some Fe$^{II}$NO-Hb. After 72 minutes, 24% of the Hb is of the Fe$^{II}$NO-Hb form, and 74% is MetHb, 30% of which has nitrite bound.

Figure 4A:
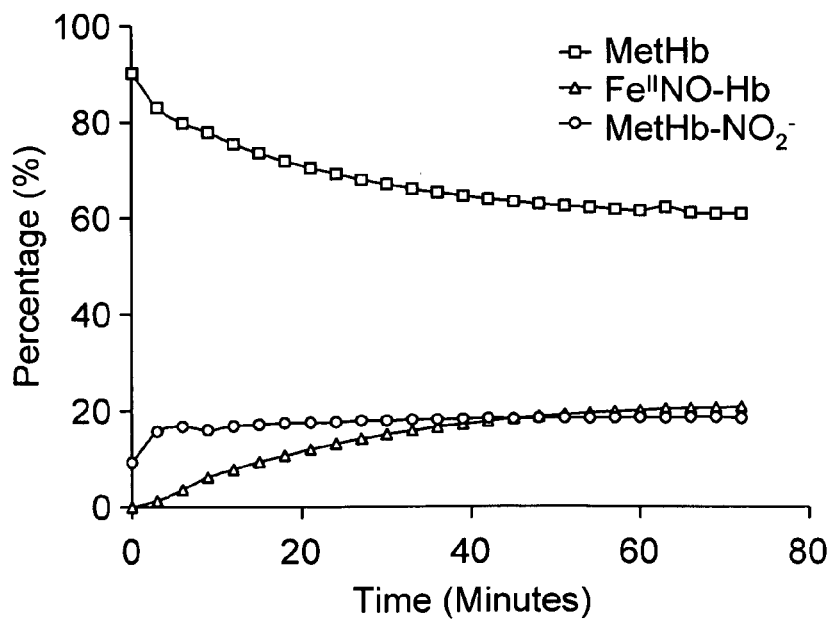
FIG. 4. The reaction between MetHb with Angeli's salt. 4A: MetHb (100 μM) was mixed with 100 μM Angeli's salt in 0.1 M phosphate buffer equilibrated in aerobic conditions. Each spectrum was fit to basis spectra to determine the percentage of each species at each time point. After 72 minutes, we found there to be 20%±2% $Fe^{II}NO$-Hb, 64%±3% MetHb, and 15%±5% $MetNO_2^-$ (n=3). 4B: MetHb (100 μM) was mixed with 100 μM Angeli's salt in 0.1 M phosphate buffer equilibrated in anaerobic conditions. Each spectrum was fit to basis spectra to determine the percentage of each species at each time point. After 72 minutes, we found there to be 54%±5% $Fe^{II}NO$-Hb, 16%±9% MetHb, 22%±3% $MetNO_2^-$ (n=3).

The Fe$^{II}$NO-Hb detected when mixing AS with OxyHb is likely to be due to the reaction of MetHb initially produced with HNO. To confirm this, we reacted equimolar amounts (100 µM) of AS and MetHb (FIG. 4A) under aerobic conditions. Since one AS will convert two OxyHb to two MetHb with two-fold excess AS to OxyHb, it was expected that more than 24% of the Hb would be converted to Fe$^{II}$NO-Hb after 72 minutes in FIG. 3 and more than 20% of the Hb would be converted to Fe$^{II}$NO-Hb after 72 minutes in FIG. 4A.

Figure 4B:
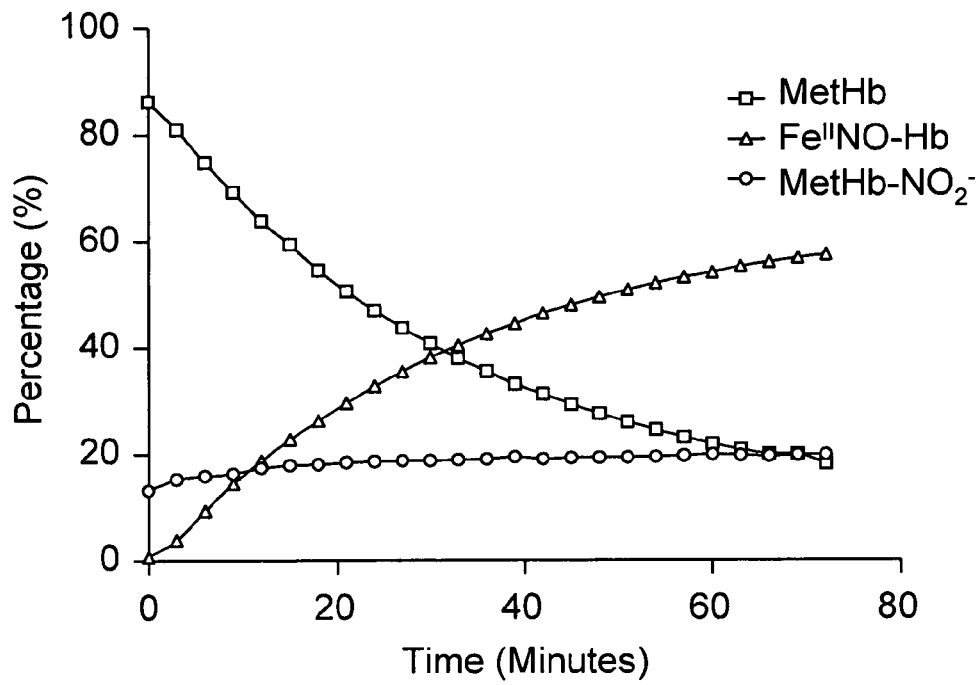

A likely reason for the lower yield is that some of the Fe$^{II}$NO-Hb was converted back to MetHb via reactions involving oxygen (see Arnold et al., Isolation and oxygenation reactions of nitrosylmyoglobins. *Methods Enzymol.* 269, 41 (1996)). These reactions are typically slow, but could contribute to Fe$^{II}$NO-Hb depletion. To test this, we allowed 270 µM Hb that was 43% Fe$^{II}$NO-Hb (formed by reaction of AS with MetHb) to sit in room air for 82 minutes and found that 29% of the Fe$^{II}$NO-Hb was converted to MetHb (data not shown). To further explore the role of oxygen in affecting Fe$^{II}$NO-Hb yield, we repeated the experiment shown in FIG. 4A, mixing 100 µM AS with 100 µM MetHb, only this time using anaerobic conditions. As shown in FIG. 4B, significantly more Fe$^{II}$NO-Hb is made (about 60% of total Hb).

Figure 5A:
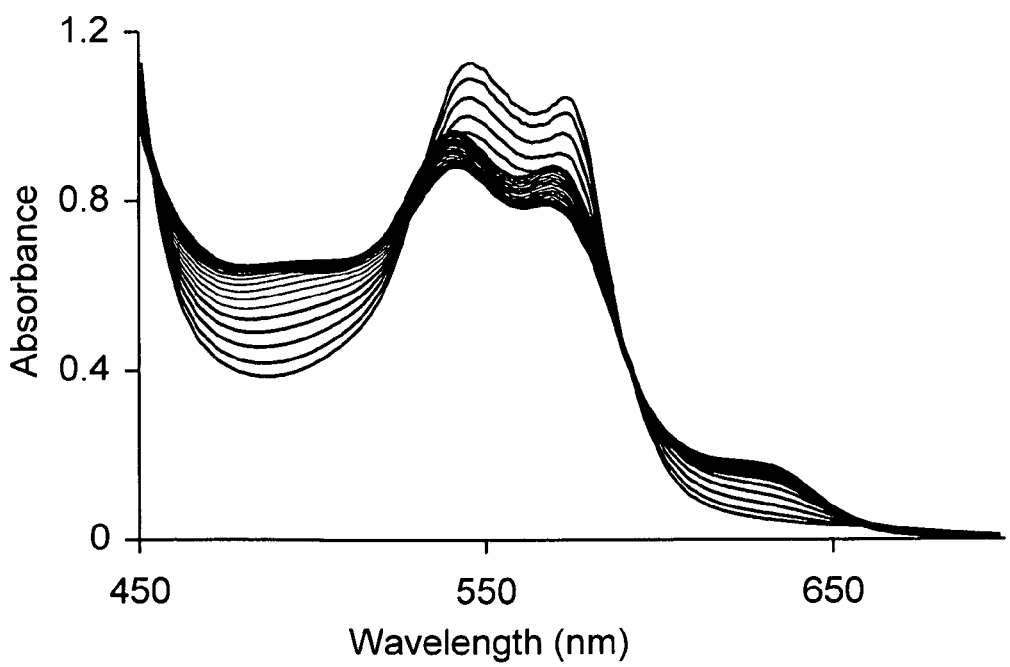
FIG. 5. The reaction between partially oxygenated hemoglobin with Angeli's salt. Partially oxygenated hemoglobin (100 μM) was mixed with 100 μM Angeli's salt in deoxygenated phosphate buffer. 5A: Raw absorption spectra. 5B: Each spectrum was fit to basis spectra to determine the percentage of each species at each time point. 5C: The average amount of each species formed at 72 minutes from three different experiments. Standard deviations are also shown.
Figure 5B:
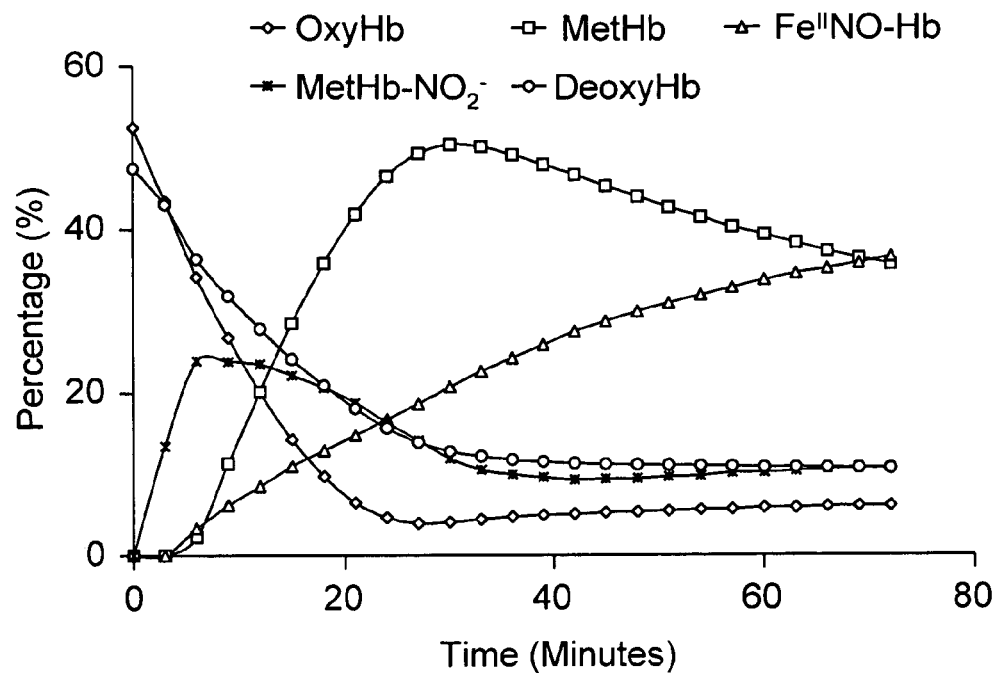
Figure 5C:
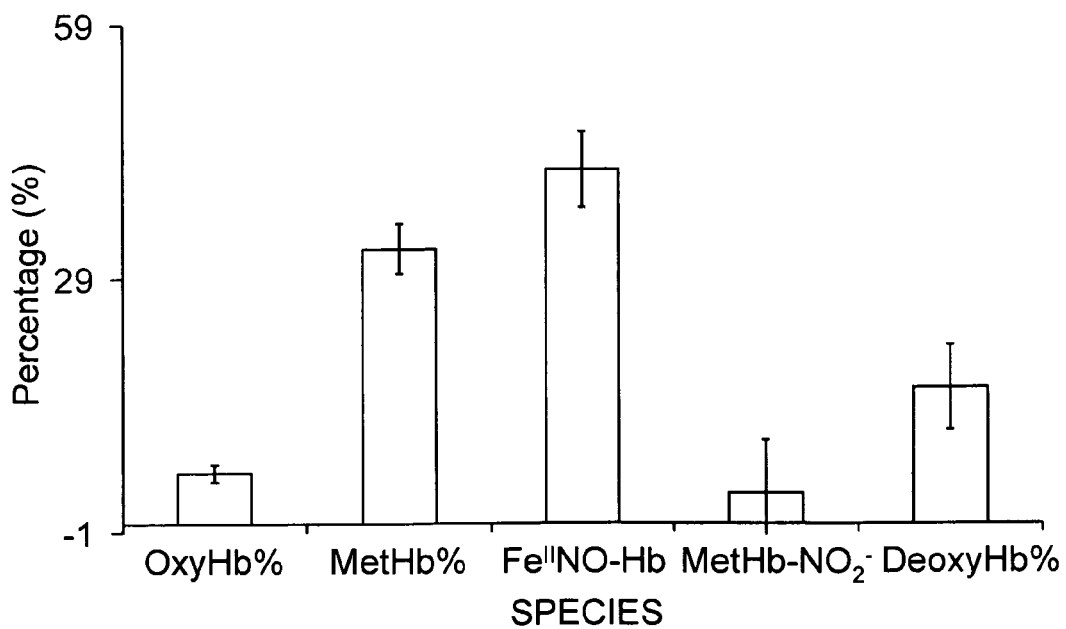

In vivo, the oxygen pressure and Hb oxygen saturation is typically less than that present when Hb is prepared in solution under aerobic conditions. Therefore, we examined the reaction of AS with partially oxygenated Hb (FIG. 5A). As shown in FIG. 5B, the percentage of MetHb in the sample rises, presumably due to the reaction with OxyHb, and then falls, most likely due the reaction of MetHb with AS to form Fe$^{II}$NO-Hb. After 72 minutes, about 45% of the sample is converted to Fe$^{II}$NO-Hb (FIG. 5C).

Figure 6A:
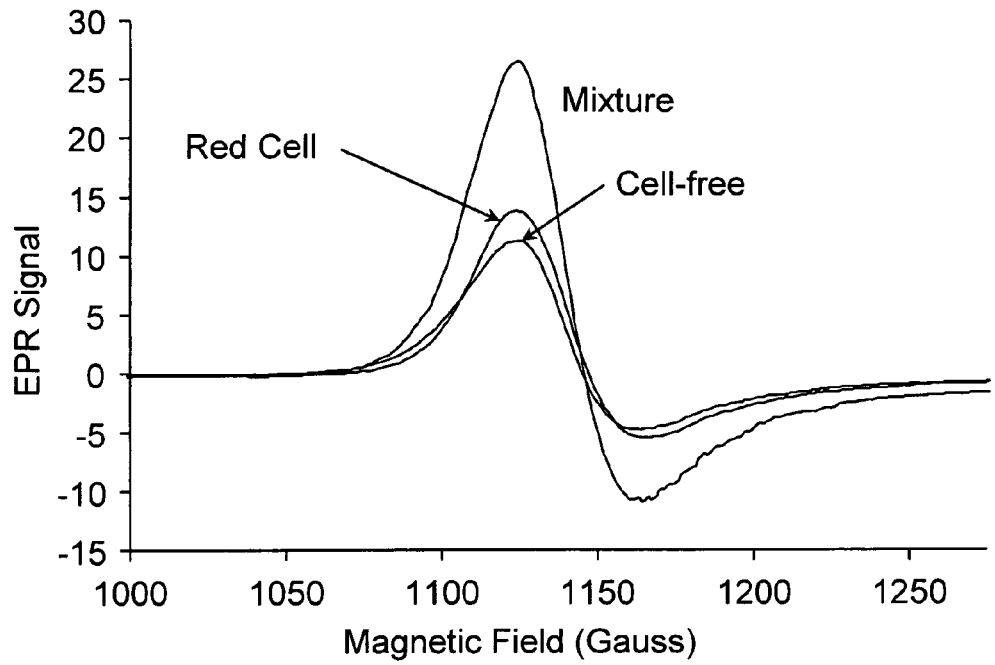
FIG. 6. Preferential reactivity of AS. 6A: Fifty micromolar AS was added to a mixture 107 μM cell-free Hb and RBCs at 41% hematocrit in aerobic conditions. After 31 minutes, the samples were analyzed for MetHb formation by EPR. Spectra are shown for the cell-free Hb and red blood cell fractions, as well as a mixture of the two. Double integration of the EPR peaks yielded 31 μM in the cell-free fraction, 36 μM in the red cell fraction, and 69 μM in the mixture. 6B: The formation of iron-nitrosyl Hb in the cell-free fraction is demonstrated using EPR spectroscopy. One spectrum was taken from a sample where 50 μM AS was added to a mixture of RBCs at 17% hematocrit and 31 μM cell-free Hb for 31 minutes resulting in 0.5 μM Fe$^{II}$NO-Hb in the cell-free fraction. The other spectrum was taken from a sample where 150 μM was added to a mixture of red cells at 16% hematocrit and 29 μM cell-free Hb resulting in the formation of 2 μM Fe$^{II}$NO-Hb. 6C: A summary of the preferential reactivity of AS is given for different conditions (data shown as average of three different preparations with error bars showing the standard deviation). The bar on the left is from data where 50 μM AS was added to red blood cells at 42±1% hematocrit and 99±7 μM cell-free Hb under completely aerobic conditions. The middle bar is from data where 50 μM AS was added to red cells at 15±1% and 102±2 μM cell-free Hb under completely aerobic conditions. The bar on the right is from when 50-150 μM AS was added to red blood cells at 16±1% hematocrit and 30±2 μM cell-free Hb under partially anaerobic conditions, so that Hb oxygen saturation was 68±12%.

FIG. 6 shows that AS preferentially reacts with cell-free Hb compared to RBC encapsulated Hb. As described above, competition experiments were performed where AS was added to a mixture of red cells and cell-free Hb, and the relative rate of the reaction was monitored examining the products in each fraction after separation by sedimentation. FIG. 6A shows EPR spectra taken from a mixture of 50 μM AS with 107 μM cell-free Hb and red cells at a hematocrit of 41% (corresponding to about 10 mM in Hb) after 30 minutes of incubation under aerobic conditions. Under these conditions, MetHb is the only product of AS/HbO$_2$ reaction. Spectra are shown for the cell-free Hb (supernatant), red-cell encapsulated Hb (pellet), and the whole mixture (before sedimentation). The sum of the MetHb in each fraction is equal to that in the whole mixture and this condition was used as a self-consistency check for inclusion of data sets for calculating the preferential reactivity, $k_f/k_r$.

Figure 6B:
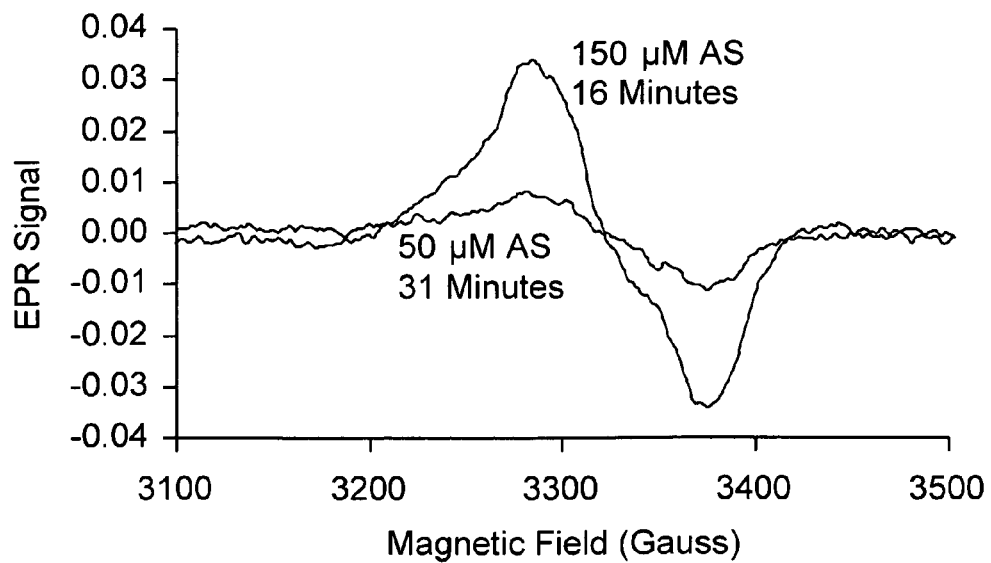
Figure 6C:
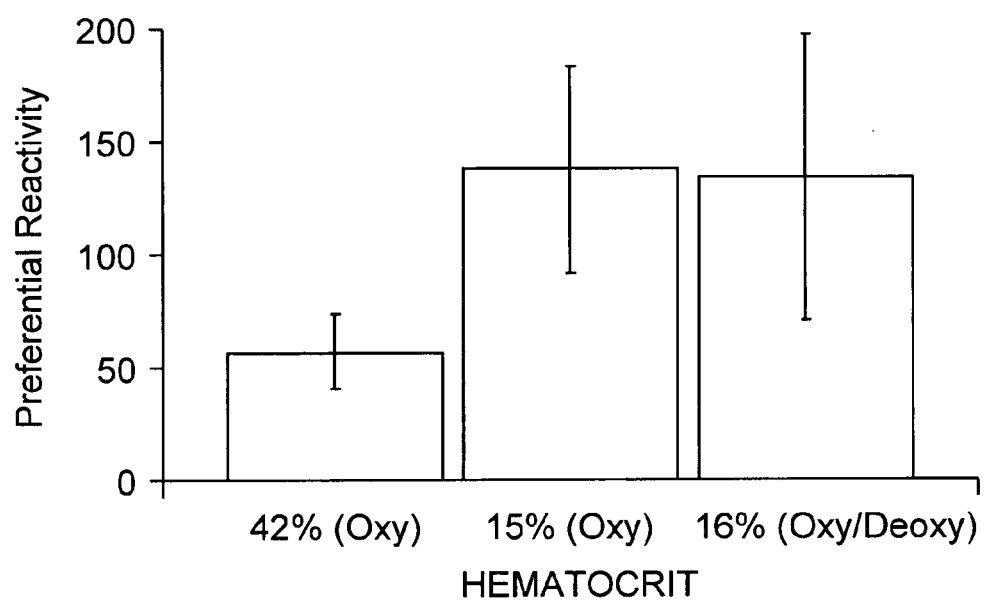

Since there was about 100 times more RBC-encapsulated Hb than cell-free Hb, if AS had no preferential reactivity ($k_f/k_r=1$), one would expect only 1% of the MetHb formed by reaction with AS to be in the cell-free Hb fraction. Instead, 45% of the reacted Hb is in the cell free fraction, giving a value of $k_f/k_r=75$. When the ratio of AS to cell-free Hb increases and the system is partially deoxygenated, iron-nitrosyl Hb is detected both in the cell-free fraction and RBC-encapsulated fraction (FIG. 6B). FIG. 6C shows a summary of the preferential reactivity of AS from multiple trials under different conditions. The preferential reactivity is greater for lower hematocrits (such as in hemolytic anemias), as has been observed previously for NO (Azarov et al., Nitric oxide scavenging by red blood cells as a function of hematocrit and oxygenation. *J. Biol. Chem.* 280 (47), 39024 (2005)).

In summary, the results were as follows: (1) AS is efficient at converting OxyHb to MetHb, and a significant portion of this has nitrite bound, (2) AS will further convert MetHb to Fe$^{II}$NO-Hb under physiologically or pathophysiologically relevant conditions, and (3) AS preferentially reacts with cell-free Hb compared to RBC encapsulated Hb. These results suggest that AS administration is useful in the context of reducing NO scavenging by cell-free Hb in pathological conditions associated with hemolysis.

Previous work has reported the rapid reaction of HNO released from AS with OxyHb to form MetHb (Doyle et al., Oxidation and Reduction of Hemoproteins by Trioxodinitrate (Ii)—the Role of Nitrosyl Hydride and Nitrite. *J Am Chem Soc* 110 (2), 593 (1988); Miranda et al., A biochemical rationale for the discrete behavior of nitroxyl and nitric oxide in the cardiovascular system. *Proc. Natl. Acad. Sci. USA* 100 (16), 9196 (2003); Miranda et al., Comparison of the reactivity of nitric oxide and nitroxyl with heme proteins—A chemical discussion of the differential biological effects of these redox related products of NOS. *J Inorg Biochem* 93 (1-2), 52 (2003)). The pathway likely involves an electron donation of nitroxyl to the bound dioxygen,

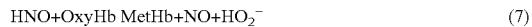
HNO+OxyHb MetHb+NO+HO$_2^-$ (7)

The NO formed can then react with another OxyHb to form MetHb and nitrate, giving the relation of Scheme 4, where one AS-derived HNO converts two OxyHb to two MetHb. Our results shown in FIG. 2 are consistent with this stoichiometry. In addition, we find that about 10% of the MetHb has nitrite bound to it. Although the formation of MetHb-NO$_2^-$ has not been reported before, the result is consistent with observations that AS forms nitrite and MetHb binds nitrite (Rodkey, Mechanism for Conversion of Oxyhemoglobin to Methemoglobin by Nitrite. *Clin. Chem.* 22 (12), 1986 (1976)). MetHb-NO$_2^-$ is less likely to cause oxidative damage than MetHb alone.

FIGS. 3, 4 and 5 show the formation of Fe$^{II}$NO-Hb. The kinetics of the reaction of HNO with OxyHb to form MetHb is about ten times faster than the reaction of HNO with MetHb to form Fe$^{II}$NO-Hb. Thus, one expects to convert most of the OxyHb to MetHb before MetHb is converted to Fe$^{II}$NO-Hb. This is what is observed in FIGS. 3 and 5. We have shown that more Fe$^{II}$NO-Hb is made when oxygen tension is lowered (FIGS. 4 and 5), most likely due to the reaction of oxygen with Fe$^{II}$NO-Hb to form MetHb. Formation of Fe$^{II}$NO-Hb, which will be enhanced under conditions with lower oxygen tension, will benefit patients in that it is a relatively stable, non-toxic form of Hb.

Other reactions besides those discussed so far may also be considered to play a role when AS is added to OxyHb. First, AS-derived nitrite may react with the OxyHb, but that reaction is too slow to be a significant factor, which we confirmed by adding nitrite to OxyHb and observing very little reaction. The reaction of nitrite with deoxyHb to form MetHb and NO could play some role. This reaction is fastest (6 M$^{-1}$s$^{-1}$) when a sample is partially oxygenated so that some of the material is in the R quaternary state, but still much slower than the reaction of HNO with OxyHb (Huang et al., Enzymatic function of hemoglobin as a nitrite reductase that produces Nitric oxide under allosteric control. *J. Clin. Invest.* 115, 2099 (2005); Huang et al., The Reaction Between Nitrite and Deoxyhemoglobin: Reassment of Reaction Kinetics and Stoichiometry. *J. Biol. Chem.* 280, 31126 (2005)). Thus, the reaction of nitrite with deoxyHb could make some, but not a great, contribution to the yields we observed. Another reaction to consider would be the result of NO (formed from reaction of HNO with OxyHb) binding to MetHb. Since the dissociation rate of NO from MetHb is fast (about 1 s$^{-1}$) and the association rate is slow (4×10$^3$ M$^{-1}$s$^{-1}$) compared to the dioxygenation reaction and NO binding to ferrous heme (Cooper, Nitric oxide and iron proteins. *Biochim. Biophys. Acta-Bioenerg.* 1411 (2-3), 290 (1999)), very little if any NO bound MetHb is likely to form. However, there is some possibility that a small amount that does form would undergo reductive nitrosyaltion forming deoxyHb and nitrite (Fernandez et al., Nitrite catalyzes ferriheme protein reductive nitrosylation. *J Am Chem Soc* 125 (35), 10510 (2003)).

We have shown in FIG. 6 that AS reacts preferentially with cell-free Hb compared to that encapsulated in the red cell. That the preferential reactivity ($k_f/k_r$) is higher for lower hematocrit demonstrates that a large factor in establishing the preferential reactivity is that the reaction with red cell encapsulated Hb is rate-limited by the time it takes for the HNO to diffuse into the red blood cell, similar to that described for NO (Azarov et al., Nitric oxide scavenging by red blood cells as a function of hematocrit and oxygenation. *J. Biol. Chem.* 280 (47), 39024 (2005)). The values of $k_f/k_r$ found here for AS are about ⅓ smaller than those measured for NO. One possible reason for this is that the bimolecular rate for the reaction of NO with HbO$_2$ is faster than that of AS with HbO$_2$ (Huang et al., Nitric Oxide Red Blood Cell Membrane Permeability at high and low Oxygen Tension. *Nitric Oxide* 16, 209 (2007)). It has been shown both computationally (Tsoukias et al., Erythrocyte consumption of nitric oxide in presence and absence of plasma-based hemoglobin. *Am. J. Physiol.-Heart Circul. Physiol.* 282 (6), H2265 (2002)) and experimentally (Olson, Stopped-Flow, Rapid Mixing Measurements of Ligand Binding to Hemoglobin and Red Cells. *Methods Enzymol.* 76, 631 (1981)) that when the intrinsic rate of reaction of Hb with a ligand is slower, $k_f/k_r$ is smaller. Since AS releases nitrite, and nitrite reacts relatively slowly with Hb, its reactions may contribute to a smaller value of $k_f/k_r$ for AS compared that of NO. The reaction with OxyHb is very slow and probably does not contribute, but that with deoxyHb may be significant. In any case, the values of $k_f/k_r$ that we measured were quite large (about 50 at 42% hematocrit and 130 at 16% hematocrit).

Under partially oxygenated conditions, we measured $Fe^{II}NO$-Hb in both the cell-free and red cell fractions when performing competition experiments. The $Fe^{II}NO$-Hb formed under these conditions could be from the reaction of (1) MetHb with HNO or (2) from the HNO with OxyHb to form MetHb and NO with subsequent binding of NO to deoxyHb. The amount of $Fe^{II}NO$-Hb made in the cell-free fraction was limited probably due to the fact the reaction of HNO with cell-free MetHb does not have great preferential reactivity compared to the reaction with red cell OxyHb (or other Hb red cell reactions which are rate-limited by diffusion to the red cell). One may expect the cell-free $Fe^{II}NO$-Hb yield to be greater in vivo due to the cell-free zone. Due to the fact that red cells travel fastest in the middle of blood vessels, a pressure gradient is formed pushing the red cells inward creating a red-cell free zone near the endothelium (Butler et al., Diffusion of nitric oxide and scavenging by blood in the vasculature. *Biochim. Biophys. Acta* 1425 (1), 168 (1998)). In this zone, AS will only react with cell-free Hb which is not pushed to the center of the vessel.

In conclusion, we have shown that AS reacts preferentially with cell-free Hb to form MetHb and iron nitrosyl Hb. The preferential reactivity is greatest at low hematocrit as occurs in hemolytic anemias. As the products of the reaction do not effectively scavenge NO, AS is useful to treat hemolysis by restoring NO availability.

EXAMPLE 2

In Vivo Study of Angeli's Salt Administration Demonstrates a Reduction in Hemolysis Using an established canine model of intravascular hemolysis described previously (see, e.g., Minneci et al., Hemolysis-associated endothelial dysfunction mediated by accelerated NO inactivation by decompartmentalized oxyhemoglobin. *J. Clin. Invest.* 115 (12), 3409 (2005)), a total of sixteen purpose-bred beagles (12-28 months, 9-12 kg) were treated with a six-hour free water continuous infusion (16 ml/kg/h) administered via a pericutanous catheter placed in the external jugular vein. In addition to free water, each animal was randomized to receive either a concomitant 6 hour continuous infusion of Angeli's salt infusion (5, 10, or 15 mcg/kg/min) or an equivalent volume of normal saline control. So as to eliminate the potential for Angeli's salt to dilute the hypotonic effect of the free water infusion, Angeli's salt was administered via a separate catheter, placed either in the contralateral external jugular vein or a femoral vein. Plasma free hemoglobin, methemoglobin and NO consumption were measured at 1.5 hour intervals (t=0, 1.5 h, 3 h, 4.5 h and 6 h) as previously described (Minneci et al., Hemolysis-associated endothelial dysfunction mediated by accelerated NO inactivation by decompartmentalized oxyhemoglobin. *J. Clin. Invest.* 115 (12), 3409 (2005)).

Figure 7A:
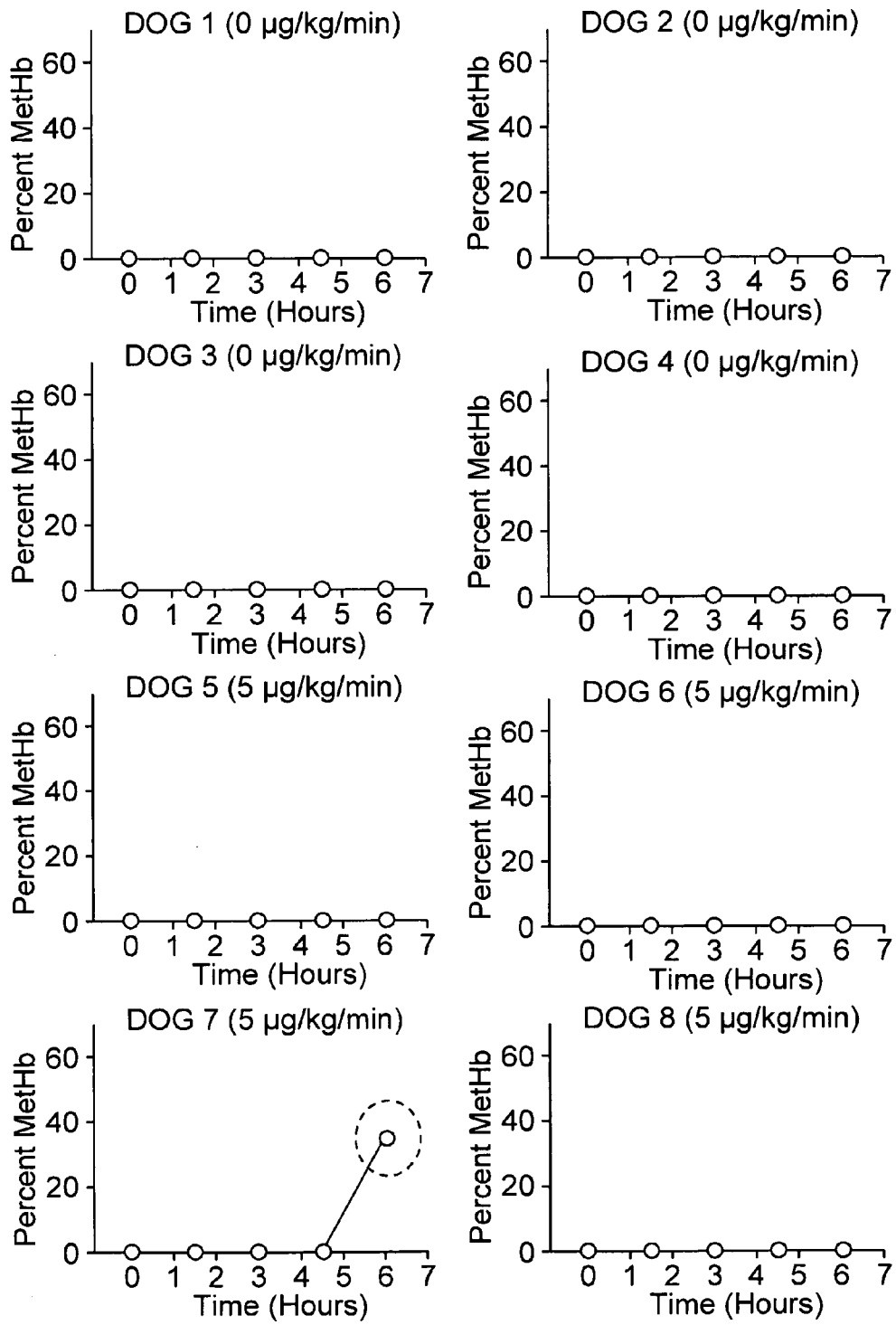
FIG. 7. Conversion of OxyHb to MetHb by AS in vivo. The percentage of MetHb compared to total Hb is plotted over time during water infusion, which causes hemolysis. The plots are made for 16 animals (labeled DOG 1-DOG 16) at four dosages of AS (0 to 15 μg/kg/min). 7A: No MetHb is seen in the zero or 5 μg/kg/min dosages, with the single outlier at six hours for DOG 7. 7B: MetHb is seen at 10 and 15 μg/kg/min dosages, and increases with the higher dose.
Figure 7B:
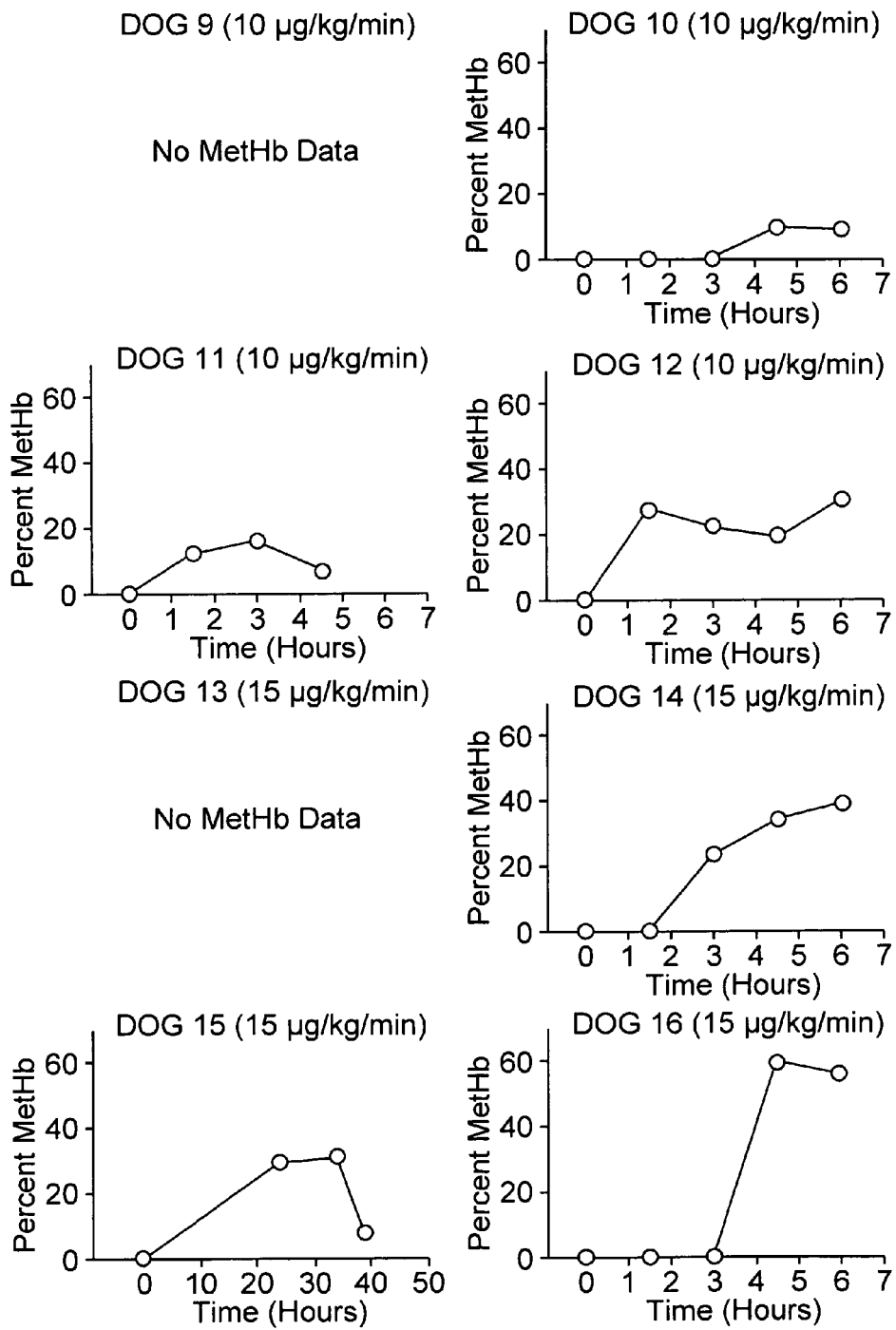

The ability of AS to convert cell-free NO scavenging OxyHb to non-NO scavenging MetHb in vivo is demonstrated in FIG. 7. Water was infused into dogs to induce hemolysis, and varying infusion rates of AS were also administered (0 to 15 µg/kg/min). At the lowest doses (0 and 5 µg/kg/min), the percentage of cell-free Hb converted to MetHb was not significant. However, at higher doses, a higher percentage of MetHb was formed. As shown in FIG. 7, no MetHb is seen in the zero or lowest dosages, with the single outlier at six hours for DOG 7, but more is seen at higher dosages, increasing with dose.

Figure 8A:
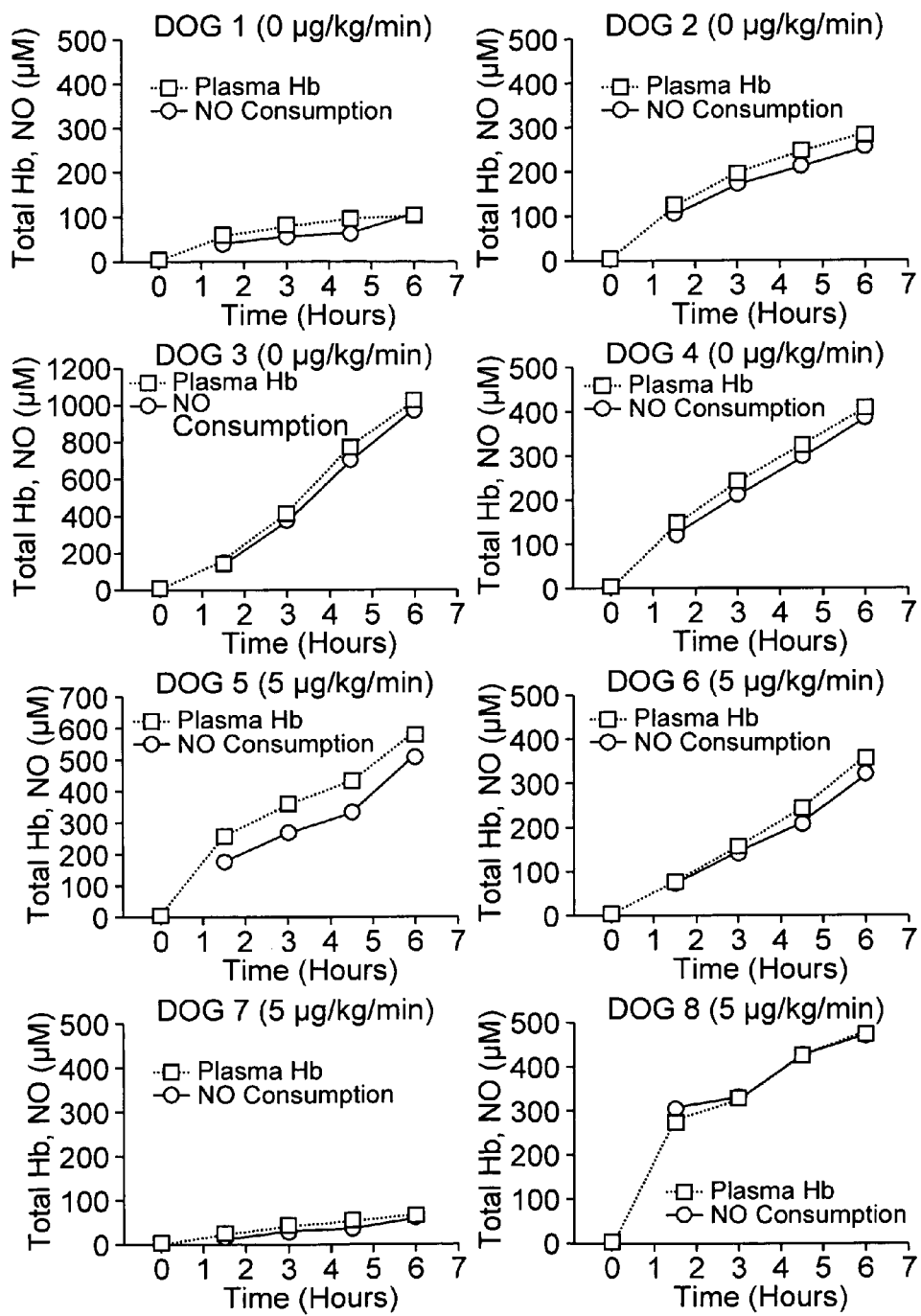
FIG. 8. AS reduces plasma Hb and NO consumption. Total plasma Hb (μM) and NO consumption (μM) were plotted for each animal as a function of time during the water infusions as in FIG. 7. The amount of total plasma Hb and NO consumption both decrease as the AS dose increases.
Figure 8B:
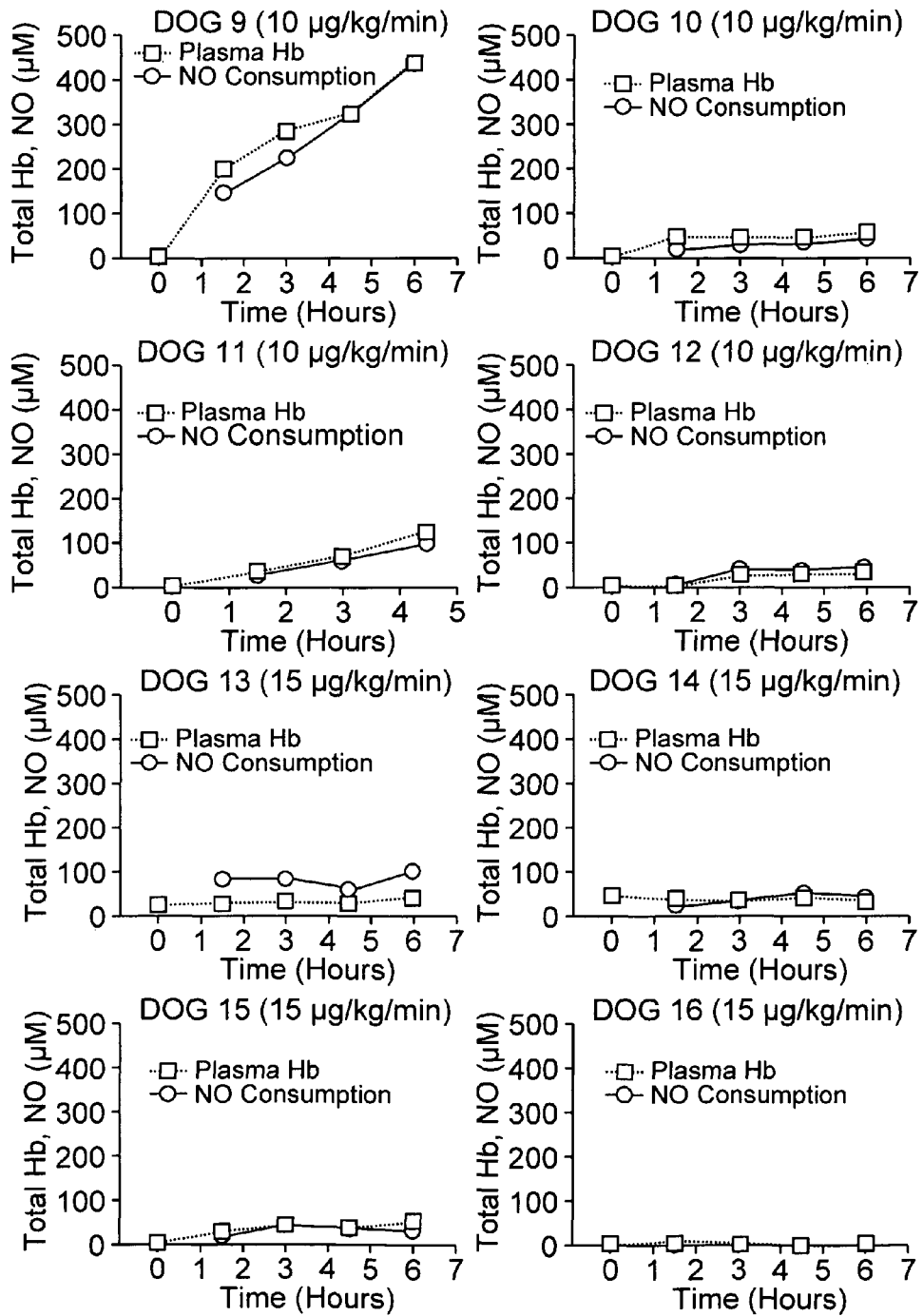

Total plasma Hb (µM) and NO consumption (µM) were plotted for each animal as a function of time during the water infusions as in FIG. 7, and these plots are shown in FIG. 8. Total plasma Hb was determined by sedimentation of red blood cells and absorption spectroscopy of the supernatant (containing only plasma (cell-free) Hb). Spectra were collected on the supernatant and the concentration was determined by fitting to basis spectra for oxygenated Hb, deoxygenated Hb, and methemoglobin (normalized by their extinction coefficients). The sum of the concentrations of all of these species is the total plasma Hb.

Our measurements did not detect $Fe^{II}NO$-Hb at these conditions. However, in these studies the amount of hemolysis is higher than what we expect in many conditions we would treat where we expect to see iron nitrosyl. It is seen in FIG. 8 that hemolysis in this canine model reaches hundreds of micromolar to millimolar quantities. Yet, as discussed above, just one micromolar cell-free Hb can reduce NO bioavailability. In sickle cell disease, the average amount of cell-free Hb is 4 µM, and this goes up a few fold in crisis, but is still much less than that shown in FIG. 8. Therefore, it should be noted that in this canine model the total amount of hemolysis induced is quite high compared to what is observed in many human conditions (hundreds of micromolar in the canine model compared to tens of micromolar or less in (for example) sickle cell disease).

FIG. 8 shows that the amount of NO consumption is seen to decrease as the AS dose increases. Intriguingly, AS administration also led to a dose-dependent reduction in levels of cell-free Hb, which is the total amount of cell-free Hb (all forms, e.g., OxyHb, MetHb, etc.). Therefore, whereas FIG. 7 shows that, as expected, the proportion of cell-free Hb that is MetHb increases as AS dose increases, FIG. 8 shows that, in addition, the total amount of plasma (cell-free) Hb is decreasing.

We ensured that the reduction in cell-free Hb is not due to a local effect on osmolarity when there is co-infusion of water and AS salt by taking care to make sure the points of infusion were separate. Without wishing to be bound by theory, the surprising result that cell-free Hb is reduced may be due a reduction in hemolysis secondary to a direct effect of AS on RBC osmotic or mechanical fragility or interaction with other compounds in the blood that lead to improved resistance to hemolysis or improved clearance (via haptoglobin or similar mechanisms).

Figure 9:
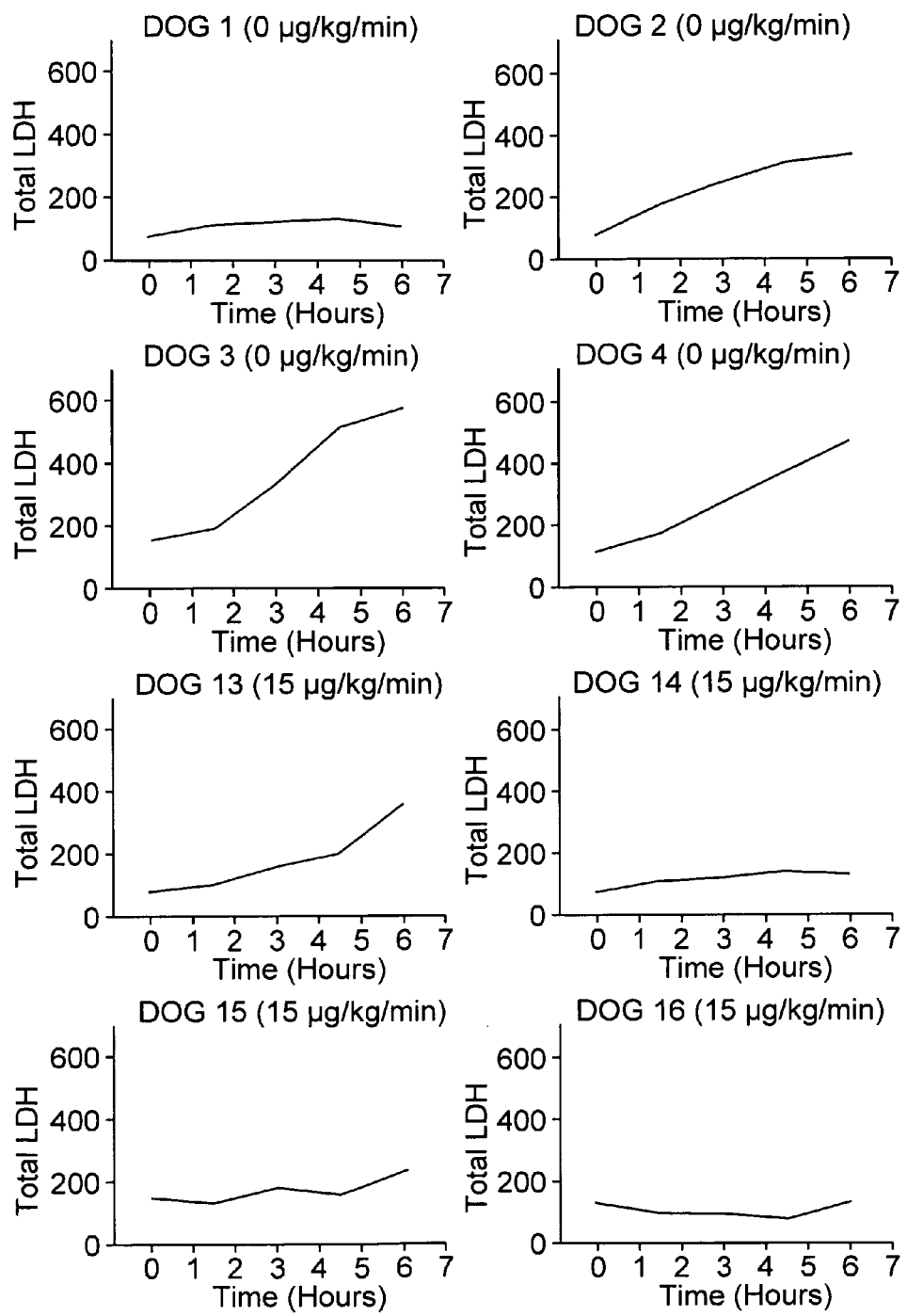

To test whether the decrease in cell-free Hb is due to a decrease in hemolysis, we measured lactate dehydrogenase (LDH), which is released from RBCs upon hemolysis and is thus used as a quantitative marker. FIG. 9 shows that LDH rises as a function of time during water infusion in the absence of AS administration, but this is much less so when AS is administered. These data suggest that AS reduces cell free Hb by reducing hemolysis rather than through increasing clearance of cell-free Hb.

Figure 10:
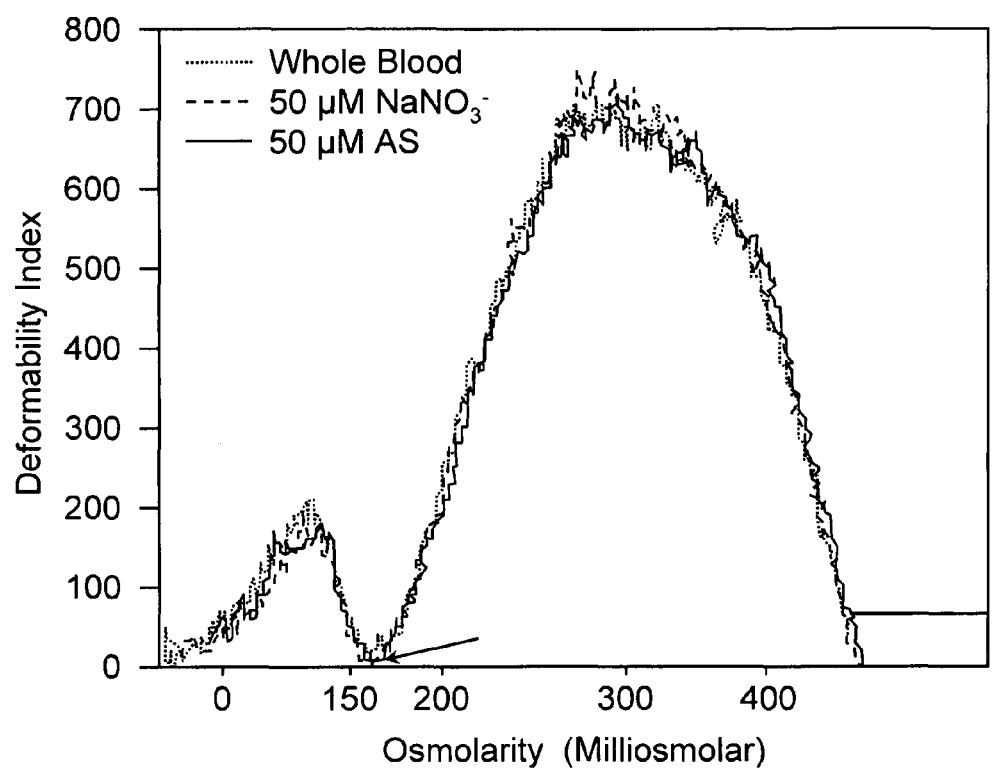
FIG. 10. Typical osmoscan examining influence of AS. Blood is diluted into a viscous fluid and placed in an ektacytometer (see Clark et al., Osmotic Gradient Ektacytometry—Comprehensive Characterization of Red-Cell Volume and Surface Maintenance, *Blood* 61 (5): 899-910 (1983)). The deformability index is plotted against osmolarity. The peak in deformability appears at 290 milliosmolar, as expected. As the osmolarity is decreased from this maximum, the red blood cells swell and their deformabilities decrease until they lyse (indicated by arrow). The osmolarity where the cells lyse indicates the osmotic fragility. No effect of AS on osmotic fragility of the red blood cells is seen, as curves measured with AS, nitrate (NaNO$_3^-$), and control (whole blood) are virtually identical.

To test whether this effect is due to a direct effect on osmotic fragility, we performed tests on osmotic fragility of RBCs incubated with varying amounts of AS. We employed laser assisted ekatacytometry as a function of osmotic strength (see Clark et al., Osmotic Gradient Ektacytometry—Comprehensive Characterization of Red-Cell Volume and Surface Maintenance, *Blood* 61 (5): 899-910 (1983)). The blood is placed between two concentric cylinders, and shear is induced by rotating one cylinder with respect to the other. The shear causes the cells to deform, and the degree of deformation is measured by analysis of the diffraction pattern made by an incident laser beam. The more deformed the cells, the more elliptical the pattern. The ellipticity of the pattern is quantified in terms of a deformability index as plotted in FIG. 10. The deformability is characteristically greatest at isotonic osmolarity (290 milliosmolar) and decreases at lower osmlarities due to cell swelling or at higher osmolarities due to cell dehydration. When the osmolarity is lowered enough, the cells lyse and this point (indicated by the arrow in FIG. 10) is a measurement of the osmotic fragility. In the representative data shown in FIG. 10, it is seen that AS has no direct effect on osmotic fragility. We performed these studies on blood from three non-patient volunteers and one patient with sickle cell disease and saw no effect of using 50, 100, or 200 µM AS at room temperature or 37 degrees Celsius at any of several shear stress values we applied. From these results, it appears that the effect of AS on the level of cell-free Hb in our canine model is not due to a direct effect on osmotic fragility. It remains possible that AS activates something in vivo that then affects osmotic fragility.

It should be noted, as well, that this canine model of hemolysis differs from human pathophysiology found in some conditions associated with hemolysis in that in the canine model hemolysis is likely due to altered local osmolarity due to the water infusion, whereas in human pathophysiology, other causes such as altered red cell rheology or immunolgical reactions often cause hemolysis. Though care was taken in developing the canine model of hemolysis, it cannot be ruled out that the observed reduction in hemolysis was due to a mechanism of hemolysis that is particular to this in vivo model.

In summary, we have demonstrated that AS will inactivate the NO scavenging ability of cell-free Hb in an in vivo (dog) model. Furthermore, as the AS dose was increased, the reduction in NO consumption was paralleled by a reduction in the amount of cell-free Hb (plasma Hb). Still further, it was discovered that there was a decrease in hemolysis associated with the decrease in cell-free Hb. Additional studies showed that the effect of AS in reducing hemolysis was not due changing the osmolarity of the plasma, either locally or systemically, or due to an effect on osmotic fragility.

That which is claimed is:

1. A method of treating hemolytic anemia in a subject in need thereof, said method comprising: administering a nitroxyl donor to said subject in an amount sufficient to treat said hemolytic anemia, wherein said nitroxyl donor donates a nitroxyl that:
    a) preferentially reacts with cell-free OxyHb, as compared to OxyHb encapsulated in a red blood cell; and
    b) reacts with MetHb to form iron-nitrosyl Hb or nitrite bound MetHb,
    wherein said nitroxyl donor is selected from the group consisting of: Angeli's salt ($Na_2N_2O_3$), isopropylamine diazeniumdiolate, and Piloty's acid ($PhSO_2NHOH$).

2. The method of claim 1, wherein said administering results in a reduction of the total amount of cell-free Hb in blood plasma.

3. The method of claim 1, wherein said nitroxyl donor is Angeli's salt.

4. The method of claim 1, wherein said administering step is carried out by parenteral administration.

5. The method of claim 1, wherein said administering step is carried out by intravenous administration.

6. The method of claim 1, wherein said administering step is carried out by transdermal administration.

7. The method of claim 1, wherein said administering step is carried out by oral administration.

8. The method of claim 1, wherein said hemolytic anemia is selected from the group consisting of: sickle cell disease, paroxysmal nocturnal hemoglobinuria, thalassemia intermedia, malaria, thrombotic thrombocytopenic pupura, hemolytic uremic syndrome, and anemia associated with cardiopulmonary bypass.

9. The method of claim 1, further comprising administering to said subject: (i) red blood cells or (ii) an agent that promotes hematopoiesis.

10. A method of treating hemolytic anemia in a subject in need thereof, said method comprising: administering a nitroxyl donor to said subject in an amount sufficient to treat said hemolytic anemia, while concurrently administering a nitric oxide donor, wherein said nitroxyl donor donates a nitroxyl that:
    a) preferentially reacts with cell-free OxyHb, as compared to OxyHb encapsulated in a red blood cell; and
    b) reacts with MetHb to form iron-nitrosyl Hb or nitrite bound MetHb,
    wherein said nitroxyl donor is selected from the group consisting of: Angeli's salt ($Na_2N_2O_3$), isopropylamine diazeniumdiolate, and Piloty's acid ($PhSO_2NHOH$).

11. The method of claim 10, wherein said nitric oxide donor comprises NONOate.

12. The method of claim 10, wherein said nitric oxide donor comprises spermine NONOate.

13. The method of claim 10, wherein said administering results in a reduction of the total amount of cell-free Hb in blood plasma.

14. The method of claim 10, wherein said nitroxyl donor is Angeli's salt.

15. The method of claim 10, wherein said hemolytic anemia is selected from the group consisting of: sickle cell disease, paroxysmal nocturnal hemoglobinuria, thalassemia intermedia, malaria, thrombotic thrombocytopenic pupura, hemolytic uremic syndrome, and anemia associated with cardiopulmonary bypass.

16. A method of treating hemolytic anemia in a subject in need thereof, comprising administering Angeli's salt to said subject in an amount sufficient to treat said hemolytic anemia, wherein Angeli's salt donates a nitroxyl that:
    a) preferentially reacts with cell-free OxyHb, as compared to OxyHb encapsulated in a red blood cell; and
    b) reacts with MetHb to form iron-nitrosyl Hb or nitrite bound MetHb,
    wherein the administering results in a reduction of the total amount of cell-free Hb in blood plasma of said subject.

17. The method of claim 16, wherein the administering results in a reduction of hemolysis in said subject.

* * * * *